US012274262B2

(12) United States Patent
Nyambo et al.

(10) Patent No.: US 12,274,262 B2
(45) Date of Patent: *Apr. 15, 2025

(54) DISPENSER AND METHOD OF USE THEREOF

(71) Applicant: S.C. JOHNSON & SON, INC., Racine, WI (US)

(72) Inventors: Calistor Nyambo, Mt. Pleasant, WI (US); Max Krakauer, Bay View, WI (US); Caitlin Y. O'Gara, Milwaukee, WI (US); Todd Ulrich, Racine, WI (US); Dirk K. Nickel, Mukwonago, WI (US)

(73) Assignee: S. C. JOHNSON & SON, INC., Racine, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/403,519

(22) Filed: Jan. 3, 2024

(65) Prior Publication Data

US 2024/0138404 A1    May 2, 2024

Related U.S. Application Data

(63) Continuation of application No. 17/111,855, filed on Dec. 4, 2020.

(Continued)

(51) Int. Cl.
*A01N 25/34* (2006.01)
*A01M 1/20* (2006.01)
*A01N 53/00* (2006.01)

(52) U.S. Cl.
CPC ........... *A01N 25/34* (2013.01); *A01M 1/2055* (2013.01); *A01N 53/00* (2013.01)

(58) Field of Classification Search
CPC ........ A01N 25/08; A01N 25/18; A01N 25/34; A01M 1/2055; A01M 29/12; A61L 9/042; A61L 9/127
See application file for complete search history.

(56) References Cited

U.S. PATENT DOCUMENTS 3,685,734 A    8/1972  Paciorek
3,807,082 A    4/1974  Hautmann
(Continued)

FOREIGN PATENT DOCUMENTS

CN    2562588 Y    7/2003
CN    1134269 C    1/2004
(Continued)

OTHER PUBLICATIONS

International Search Report from corresponding PCT Application No. PCT/US2020/063344, mailed Apr. 8, 2021 (3 pages).

(Continued)

*Primary Examiner* — Joshua J Michener
*Assistant Examiner* — Henry Hooper Mudd
(74) *Attorney, Agent, or Firm* — Quarles & Brady LLP

(57) ABSTRACT

A substrate for emitting a volatile material, the substrate comprising a first woven layer, a second woven layer, and a third layer. The first woven layer has a first weave pattern. The second woven layer has a second weave pattern that is different than the first weave pattern. The third layer is disposed between the first woven layer and the second woven layer. Further, the substrate is configured to provide a steady state weight loss of the volatile material between about 1 mg/day and about 10 mg/day over a time of at least 30 days.

21 Claims, 26 Drawing Sheets

Related U.S. Application Data

(60) Provisional application No. 62/944,748, filed on Dec. 6, 2019.

(56) References Cited

U.S. PATENT DOCUMENTS

| | | |
|---|---|---|
| D246,319 S | 11/1977 | Rabussier |
| 4,094,119 A | 6/1978 | Sullivan |
| 4,155,500 A | 5/1979 | Dutcher |
| D254,929 S | 5/1980 | Butcher |
| 4,208,012 A | 6/1980 | Dutcher |
| 4,277,024 A | 7/1981 | Spector |
| 4,305,892 A | 12/1981 | Hallberg |
| 4,306,892 A | 12/1981 | Atalla |
| D262,652 S | 1/1982 | Jaeschke |
| 4,361,279 A | 11/1982 | Beacham |
| 4,660,763 A | 4/1987 | Gutkowski |
| RE32,513 E | 10/1987 | Seaber et al. |
| 4,804,142 A | 2/1989 | Riley |
| 5,000,987 A | 3/1991 | Ninomiya et al. |
| 5,071,704 A | 12/1991 | Fischel-Ghodsian |
| 5,148,983 A | 9/1992 | Muniz |
| 5,150,722 A | 9/1992 | Rutherford |
| 5,304,358 A | 4/1994 | Hoyt |
| 5,455,043 A | 10/1995 | Fischel-Ghodsian |
| 5,460,787 A | 10/1995 | Colon |
| 5,468,447 A | 11/1995 | Bermas |
| 5,547,636 A | 8/1996 | Vick |
| 5,611,486 A | 3/1997 | Paul |
| 5,704,832 A | 1/1998 | Borrell |
| 5,738,831 A | 4/1998 | Bethel |
| 5,752,658 A | 5/1998 | Gibbs |
| 5,943,816 A | 8/1999 | Hyatt |
| 5,972,290 A | 10/1999 | De Sousa |
| 6,102,660 A | 8/2000 | Lee |
| 6,327,813 B1 | 12/2001 | Ishiwatari |
| 6,346,143 B1 | 2/2002 | McGowan |
| 6,386,971 B1 | 5/2002 | Johnson |
| D491,257 S | 6/2004 | Picken, Jr. |
| 6,746,521 B2 | 6/2004 | Canfield |
| 6,887,007 B2 | 5/2005 | Sorrell |
| 6,899,281 B1 | 5/2005 | Griese |
| D508,285 S | 8/2005 | Velicescu |
| D522,640 S | 6/2006 | Miro |
| 7,182,540 B2 | 2/2007 | Sorrell |
| 7,188,780 B2 | 3/2007 | Martens, III |
| 7,213,770 B2 | 5/2007 | Martens, III et al. |
| D544,590 S | 6/2007 | Yoo |
| D551,333 S | 9/2007 | Wu |
| D570,980 S | 6/2008 | Isono |
| 7,380,370 B2 | 6/2008 | Livingston |
| 7,426,799 B2 | 9/2008 | Christianson et al. |
| 7,441,360 B2 | 10/2008 | Christianson et al. |
| 7,465,116 B2 | 12/2008 | Sorrell |
| 7,523,577 B2 | 4/2009 | Majerowski |
| 7,528,102 B2 | 5/2009 | Barthel |
| 7,607,250 B2 | 10/2009 | Leonard |
| D606,642 S | 12/2009 | Weggelaar |
| 7,665,238 B2 | 2/2010 | Majerowski |
| D613,391 S | 4/2010 | Schwartz |
| D614,278 S | 4/2010 | Schwartz |
| 7,770,817 B2 | 8/2010 | Macor |
| D646,769 S | 10/2011 | Angel |
| D650,891 S | 12/2011 | Freeborn |
| D662,251 S | 6/2012 | Wauters |
| D666,284 S | 8/2012 | Robinson |
| 8,268,764 B2 | 9/2012 | Glenn, Jr. et al. |
| 8,336,145 B2 | 12/2012 | Dever et al. |
| D673,666 S | 1/2013 | Gordon |
| D675,307 S | 1/2013 | Freeborn |
| 8,349,341 B2 | 1/2013 | Glenn, Jr. et al. |
| 8,361,409 B2 | 1/2013 | Rico |
| 8,367,011 B2 | 2/2013 | Yamamoto |
| D692,546 S | 10/2013 | Gordon |
| 8,740,110 B2 | 6/2014 | Gruenbacher |
| 8,870,165 B2 | 10/2014 | Scolari |
| 8,920,734 B2 | 12/2014 | Furner et al. |
| D723,150 S | 2/2015 | Furner |
| 8,968,647 B2* | 3/2015 | Fischer ............... A61L 9/00 |
| 9,022,035 B2 | 5/2015 | Asada et al. |
| 9,192,690 B2 | 11/2015 | Zobele |
| 9,204,741 B2 | 12/2015 | Kunesh |
| 9,205,163 B2 | 12/2015 | Westphal |
| 9,248,210 B2 | 2/2016 | Kunesh |
| 9,265,853 B2 | 2/2016 | Scott et al. |
| 9,278,151 B2 | 3/2016 | Westphal |
| 9,308,401 B2 | 4/2016 | Asada et al. |
| 9,352,064 B2 | 5/2016 | Furner et al. |
| 9,629,937 B2 | 4/2017 | Lackey et al. |
| 9,675,723 B2 | 6/2017 | Chew |
| 9,694,218 B2 | 7/2017 | Asada et al. |
| 9,717,814 B2 | 8/2017 | Walter |
| D798,430 S | 9/2017 | Nord |
| 9,757,490 B2* | 9/2017 | Santini ............... A24F 25/00 |
| 10,010,642 B2 | 7/2018 | Westphal |
| D837,355 S | 1/2019 | Gunnefur |
| D843,553 S | 3/2019 | Kim et al. |
| 10,324,007 B2 | 6/2019 | Thompson |
| 2004/0057975 A1* | 3/2004 | Maleeny ............. A61L 9/015 |
| | | 424/401 |
| 2005/0089657 A1 | 4/2005 | Frandsen et al. |
| 2008/0011870 A1 | 1/2008 | Link et al. |
| 2008/0023568 A1 | 1/2008 | Weggelaar et al. |
| 2009/0317465 A1 | 12/2009 | Peppas |
| 2012/0080537 A1 | 4/2012 | Walter |
| 2013/0015265 A1 | 1/2013 | Shuval |
| 2014/0001281 A1 | 1/2014 | Slade |
| 2014/0091487 A1 | 4/2014 | Belongia |
| 2014/0141051 A1 | 5/2014 | Swanson et al. |
| 2015/0060565 A1 | 3/2015 | Furner |
| 2015/0342172 A1 | 12/2015 | Sharma et al. |
| 2015/0374871 A1* | 12/2015 | Chew ................. A61L 9/12 |
| 2016/0271287 A1 | 9/2016 | DAmico |
| 2017/0001140 A1 | 1/2017 | Lebon |
| 2017/0056914 A1 | 3/2017 | Beaumont et al. |
| 2017/0136139 A1 | 5/2017 | Seshadri et al. |
| 2017/0209613 A1 | 7/2017 | Westphal |
| 2017/0325442 A1* | 11/2017 | Kashima .............. A01M 1/20 |
| 2018/0104372 A1 | 4/2018 | McGlade et al. |
| 2018/0280557 A1 | 10/2018 | Field et al. |
| 2018/0296719 A1 | 10/2018 | Lane et al. |
| 2019/0082673 A1 | 3/2019 | Sharma et al. |
| 2019/0239501 A1 | 8/2019 | Manhas |
| 2022/0280682 A1* | 9/2022 | Bodkhe ............... A61L 15/46 |

FOREIGN PATENT DOCUMENTS

| | | |
|---|---|---|
| CN | 1391150 A | 12/2005 |
| CN | 1610500 A | 5/2007 |
| CN | 1625334 A | 5/2007 |
| CN | 101405036 A | 4/2009 |
| CN | 100581436 C | 1/2010 |
| CN | 301915942 S | 5/2012 |
| CN | 302022167 S | 8/2012 |
| CN | 302045330 S | 8/2012 |
| CN | 103189077 A | 7/2013 |
| CN | 303011915 S | 11/2014 |
| CN | 303049136 S | 12/2014 |
| CN | 303102802 S | 2/2015 |
| CN | 303161086 S | 4/2015 |
| CN | 303218922 S | 5/2015 |
| CN | 303224519 S | 5/2015 |
| CN | 104797274 A | 7/2015 |
| CN | 102958567 A | 9/2015 |
| CN | 303549821 S | 1/2016 |
| CN | 303580249 S | 2/2016 |
| CN | 303606768 S | 3/2016 |
| CN | 205357864 U | 7/2016 |
| CN | 106455534 A | 2/2017 |
| CN | 106455535 A | 2/2017 |
| CN | 304106027 S | 4/2017 |
| CN | 304306889 S | 10/2017 |
| CN | 304306890 S | 10/2017 |
| CN | 304333995 S | 10/2017 |
| CN | 107405418 A | 11/2017 |

(56) References Cited

FOREIGN PATENT DOCUMENTS

| | | |
|---|---|---|
| CN | 107530467 A | 1/2018 |
| CN | 304469181 S | 1/2018 |
| CN | 304520183 S | 2/2018 |
| CN | 304520225 S | 2/2018 |
| CN | 304565392 S | 4/2018 |
| CN | 104955489 B | 6/2018 |
| CN | 304695905 S | 6/2018 |
| CN | 304710922 S | 7/2018 |
| CN | 207911900 U | 9/2018 |
| CN | 304860828 S | 10/2018 |
| CN | 106103298 B | 11/2018 |
| CN | 105555322 B | 12/2018 |
| CN | 105705170 A | 3/2019 |
| CN | 109394551 A | 3/2019 |
| CN | 109497010 A | 3/2019 |
| CN | 110292650 A | 10/2019 |
| DM | 097747 | 12/2017 |
| DM | 097748 | 12/2017 |
| EP | 0697216 A2 | 2/1996 |
| EP | 0732946 A1 | 9/1996 |
| EP | 0835666 A2 | 4/1998 |
| EP | 0972501 A2 | 1/2000 |
| EP | 0985398 A2 | 3/2000 |
| EP | 1027874 A2 | 8/2000 |
| EP | 1077054 A2 | 2/2001 |
| EP | 1142547 A1 | 10/2001 |
| EP | 1236456 A2 | 9/2002 |
| EP | 1269949 A2 | 1/2003 |
| EP | 1297808 A2 | 4/2003 |
| EP | 1526770 A1 | 5/2005 |
| EP | 1526876 A1 | 5/2005 |
| EP | 1575471 A2 | 9/2005 |
| EP | 1620050 A2 | 2/2006 |
| EP | 1765422 A2 | 3/2007 |
| EP | 1773411 B1 | 6/2009 |
| EP | 2004024 B1 | 11/2009 |
| EP | 2130556 A1 | 12/2009 |
| EP | 2007443 B1 | 2/2010 |
| EP | 2164530 A2 | 3/2010 |
| EP | 0009103100001 | 5/2010 |
| EP | 1778302 B1 | 2/2011 |
| EP | 1979009 B1 | 10/2011 |
| EP | 2569222 A1 | 3/2013 |
| EP | 2613815 B1 | 7/2013 |
| EP | 2682133 A1 | 1/2014 |
| EP | 0023166790001 | 2/2014 |
| EP | 0023166790003 | 2/2014 |
| EP | 0023166790004 | 2/2014 |
| EP | 0023166790005 | 2/2014 |
| EP | 0023166790006 | 2/2014 |
| EP | 0023166790007 | 2/2014 |
| EP | 0023166790008 | 2/2014 |
| EP | 0023166790009 | 2/2014 |
| EP | 0023166790010 | 2/2014 |
| EP | 0023166790011 | 2/2014 |
| EP | 0023166790012 | 2/2014 |
| EP | 0023166790013 | 2/2014 |
| EP | 0024155050001 | 3/2014 |
| EP | 0024155050002 | 3/2014 |
| EP | 0024155050003 | 3/2014 |
| EP | 2355774 B1 | 6/2014 |
| EP | 2355771 B1 | 2/2015 |
| EP | 2885012 A1 | 6/2015 |
| EP | 0027187830001 | 6/2015 |
| EP | 0027187830003 | 6/2015 |
| EP | 0027187830004 | 6/2015 |
| EP | 0027187830005 | 6/2015 |
| EP | 0027187830006 | 6/2015 |
| EP | 0027187830007 | 6/2015 |
| EP | 0027187830008 | 6/2015 |
| EP | 0027187830009 | 6/2015 |
| EP | 0027187830010 | 6/2015 |
| EP | 0027187830011 | 6/2015 |
| EP | 2903654 A2 | 8/2015 |
| EP | 2925375 A1 | 10/2015 |
| EP | 2975932 A1 | 1/2016 |
| EP | 3024504 A1 | 6/2016 |
| EP | 0034160150001 | 10/2016 |
| EP | 2621546 B1 | 1/2017 |
| EP | 3169370 A1 | 5/2017 |
| EP | 0040329280001 | 6/2017 |
| EP | 0040329280009 | 6/2017 |
| EP | 2509560 B1 | 7/2017 |
| EP | 2355776 B1 | 11/2017 |
| EP | 2884873 B1 | 4/2018 |
| EP | 3348285 A1 | 7/2018 |
| IN | IN2401DEL2014 A | 8/2016 |
| JP | 2010105987 A | 5/2010 |
| JP | 2013132216 A | 7/2013 |
| JP | 2018093778 A | 6/2018 |
| MX | 2009006870 A | 7/2009 |
| MX | 2012011068 A | 10/2012 |
| MX | 2016011935 A | 4/2017 |
| MX | 2017011948 A | 2/2018 |
| MX | 357880 B | 8/2018 |
| WO | 9210933 A1 | 7/1992 |
| WO | 1990000472 A1 | 1/1999 |
| WO | 2004020004 A1 | 3/2004 |
| WO | 2005087279 A1 | 9/2005 |
| WO | 2010142469 A1 | 12/2010 |
| WO | 2011140917 A1 | 11/2011 |
| WO | 2012044659 A1 | 4/2012 |
| WO | 2014028681 A1 | 2/2014 |
| WO | 2014028682 A1 | 2/2014 |
| WO | 2014055478 A2 | 4/2014 |
| WO | 2014148999 A1 | 9/2014 |
| WO | 2015013102 A1 | 1/2015 |
| WO | 2015138892 A1 | 9/2015 |
| WO | 2015139954 A1 | 9/2015 |
| WO | 2015175527 A2 | 11/2015 |
| WO | 2015187523 A1 | 12/2015 |
| WO | 2017062485 A1 | 4/2017 |
| WO | 2017131950 A1 | 8/2017 |
| WO | 2018005423 A2 | 1/2018 |
| WO | 2018110028 A1 | 6/2018 |
| WO | 2018134079 A1 | 7/2018 |
| WO | 2018194943 A1 | 10/2018 |
| WO | 2019137621 A | 7/2019 |

OTHER PUBLICATIONS

Written Opinion of the International Searching Authority from corresponding PCT Application No. PCT/US2020/063344, mailed Apr. 8, 2021 (6 pages).

Search Strategy Report, from corresponding PCT Application No. PCT/US2020/063344, mailed Apr. 8, 2021 (1 page).

Office Action issued in corresponding ARIPO Application No. AP/P/2022/014161, dated Nov. 19, 2023.

Notification of Decision to Grant issued in corresponding Chinese Application No. 202080094447.3, dated Dec. 22, 2023.

Alejandro L. Garcia, Physics of Balance & Weight Shift, 2011, Creative Commons Attribution-Noncommerical-Share Alike 3.0, pp. 1-3, 7-8.

PCT/US2014/051586 International Search Report and Written Opinion dated Mar. 3, 2015.

Japanese Office Action from corresponding Application No. 2022-532843 dated Oct. 18, 2024, 26 pages.

* cited by examiner

DISPENSER AND METHOD OF USE THEREOF

CROSS REFERENCE TO RELATED APPLICATIONS

This application is a continuation of U.S. application Ser. No. 17/111,855, filed on Dec. 4, 2020, which claims the benefit of and priority under 35 U.S.C. § 119 to U.S. Provisional Patent Application 62/944,748, filed on Dec. 6, 2019, the entire contents of which are hereby incorporated by reference, for any and all purposes.

REFERENCE REGARDING FEDERALLY SPONSORED RESEARCH OR DEVELOPMENT

Not applicable.

SEQUENCE LISTING

Not applicable.

BACKGROUND

1. Field of the Invention

The present disclosure relates generally to a dispensing device for release of a volatile material and, more particularly, to a dispenser and substrate for the passive emanation of a volatile material that includes a multi-layer substrate supported by a protective enclosure.

2. Description of the Background

Various volatile material dispensing devices known in the art generally include a reservoir that holds a volatile material, as well as a housing or support structure that retains the reservoir. These devices typically either allow passive diffusion of the volatile material to occur without the aid of a dispensing mechanism, or enhance and/or facilitate the release of the volatile material using a dispensing mechanism. For example, typical dispensing mechanisms used in volatile material dispensing devices include a heating device and/or a fan. Such prior dispensers may often require these mechanisms or other costly materials to ensure constant release of a volatile material over a prolonged period of time; however, these prior dispensers often require electricity and are significantly more expensive to produce.

In some instances, dispensers that passively emanate a volatile material may be provided as a sheet or film, and may include a plurality of layers, one of which may be exposed to a surrounding environment and resultantly emanate an amount of volatile material therefrom. However, such prior passive dispensers also have common drawbacks. For one, a user may have to contact the material to be emanated while activating or opening the dispensing device or during use of the dispenser. Further, the release rate of active ingredients from passive dispensers typically decreases with time and the efficacy of a volatile release therefrom decreases over a period of use.

What is needed is a dispenser that preferably overcomes one or more of these drawbacks. More particularly, what is needed is a dispenser that passively emanates a volatile material over a prolonged period of time at a constant rate, while not requiring a user to contact the volatile material having active agents, such as insecticides.

SUMMARY

Embodiments of the current disclosure provide a substrate for emitting a volatile material. The substrate includes a first woven layer having a first weave pattern and a second woven layer having a second weave pattern that is different than the first weave pattern. The substrate further includes a third layer that is disposed between the first woven layer and the second woven layer. The substrate is configured to provide a steady-state weight loss of the volatile material between about 1 mg/day and about 10 mg/day over a time of at least 30 days.

In some embodiments, the volatile material includes an active agent that is applied to at least one of the first woven layer, the second woven layer, and the third layer. In some embodiments, the first weave pattern is a first honeycomb weave pattern, and the second weave pattern is a second honeycomb weave pattern.

In some embodiments, the first weave pattern includes a first weave density, the first weave density being characterized by a first plurality of fibers of the first woven layer. In some embodiments, the second weave pattern includes a second weave density, the second weave density being characterized by a second plurality of fibers of the second woven layer. In some embodiments, the second weave density is greater than the first weave density.

In some embodiments, the third layer comprises a third plurality of fibers, connecting at least one of the first plurality of fibers and the second plurality of fibers to form the substrate. In some embodiments, the third layer includes a surface density between about 75 grams per square meter and about 500 grams per square meter. In some embodiments, materials of the first and second woven layers each comprise polyester.

According to some embodiments, a substrate for emitting a volatile material comprises a first woven layer having a first weave pattern that includes a first weave density, a second woven layer having a second weave pattern that includes a second weave density, and a third layer that is disposed between the first and second woven layers. The substrate is configured to provide a steady state weight loss of the volatile material between about 1 mg/day and about 10 mg/day over a time of at least 30 days.

In some embodiments, the volatile material includes an active agent that is applied to at least one of the first woven layer, the second woven layer, and the third layer. In some embodiments, the first weave density is characterized by a first plurality of fibers of the first woven layer, and the second weave density is characterized by a second plurality of fibers of the second woven layer. In some embodiments, the second weave density is greater than the first weave density. In some embodiments, the third layer comprises a third plurality of fibers, the third plurality of fibers connecting at least one of the first plurality of fibers and the second plurality of fibers to form the substrate.

According to some embodiments, a substrate for emitting a volatile material comprises a first woven layer having a first weave pattern, a second woven layer having a second weave pattern, and a third layer that is disposed between the first woven layer and the second woven layer. The volatile material includes an active agent that is applied to at least one of the first woven layer, the second woven layer, and the third layer.

In some embodiments, the first woven layer includes a first thickness and the second layer includes a second thickness that is different than the first thickness. In some embodiments, the first weave pattern is a first honeycomb weave pattern, and the second weave pattern is a second honeycomb weave pattern. In some embodiments, the first weave pattern includes a first weave density, the first weave density being characterized by a first plurality of fibers of the first woven layer. The second weave pattern includes a second weave density, the second weave density being characterized by a second plurality of fibers of the second woven layer. In some embodiments, the first weave density is different than the second weave density.

According to some embodiments, a substrate for emitting a volatile material comprises a first woven layer, a second woven layer, and a third layer. The first woven layer has a first weave pattern that includes a first weave density. The second woven layer has a second weave pattern that includes a second weave density. The third layer is disposed between the first and second woven layers. The volatile material includes an active agent that is applied to at least one of the first woven layer, the second woven layer, and the third layer.

In some embodiments, the first weave density is characterized by a first plurality of fibers of the first woven layer and the second weave density is characterized by a second plurality of fibers of the second woven layer. The first weave density is different than the second weave density.

In some embodiments, the substrate is configured to provide a steady state weight loss of the volatile material over a period of time. In some embodiments, the period of time is at least 30 days. In some embodiments, the period of time is at least seven months. In some embodiments, the substrate has an emanation rate of between about 1 mg/day and about 10 mg/day.

DETAILED DESCRIPTION OF THE DRAWINGS

The following discussion and accompanying figures disclose various embodiments or configurations of a dispensing device and a substrate that may be used in combination with the dispensing device.

The term "about," as used herein, refers to variation in the numerical quantity that may occur, for example, through typical measuring and manufacturing procedures used for volatile dispensers or other articles of manufacture that may include embodiments of the disclosure herein; through inadvertent error in these procedures; through differences in the manufacture, source, or purity of the ingredients used to make the compositions or mixtures or carry out the methods; and the like. Throughout the disclosure, the terms "about" and "approximately" refer to a range of values ±5% of the numeric value that the term precedes.

The terms "weight percent," "wt-%," "percent by weight," "% by weight," and variations thereof, as used herein, refer to the concentration of a substance or component as the weight of that substance or component divided by the total weight, for example, of the composition or of a particular component of the composition, and multiplied by 100. It is understood that, as used herein, "percent," "%," and the like may be synonymous with "weight percent" and "wt-%."

The present disclosure is directed to dispensers and substrates for holding volatile materials. While the present disclosure may be embodied in many different forms, several specific embodiments are discussed herein with the understanding that the present disclosure is to be considered only as an exemplification of the principles of the disclosure, and it is not intended to limit the disclosure to the embodiments illustrated.

Further, the principles of the present disclosure apply to any volatile material emitted through passive emanation, and although particular examples illustrate the passive emanation of particular volatile materials (e.g., insecticides), it is envisioned that the dispensers and substrates discussed herein can be used with a variety of volatile materials. Examples of volatile materials include, but are not limited to, an insecticide, an insect repellant, an insect attractant, a fragrance, a mold or mildew inhibitor, a cleaner, a disinfectant, an air purifier, an aromatherapy scent, an antiseptic, a positive fragrance volatile material, an air-freshener, a deodorizer, or the like, and combinations thereof. Additives may also be included in the volatile materials, such as, fragrances or preservatives, as will be discussed in further detail herein.

Dispensers

Figure 1:
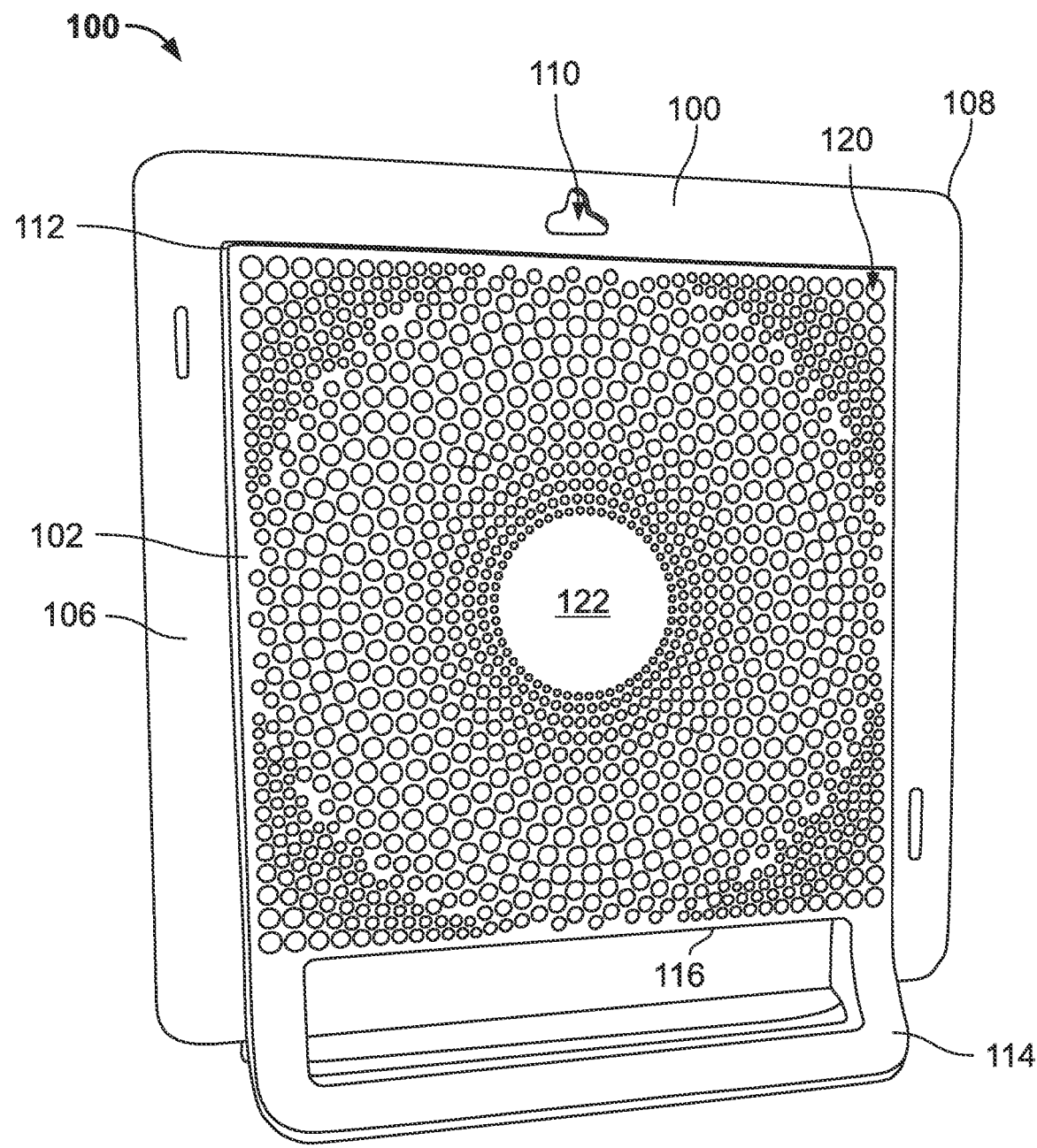
FIG. 1 is a front isometric view of a dispenser, according to a first aspect of the present disclosure.
Figure 2:
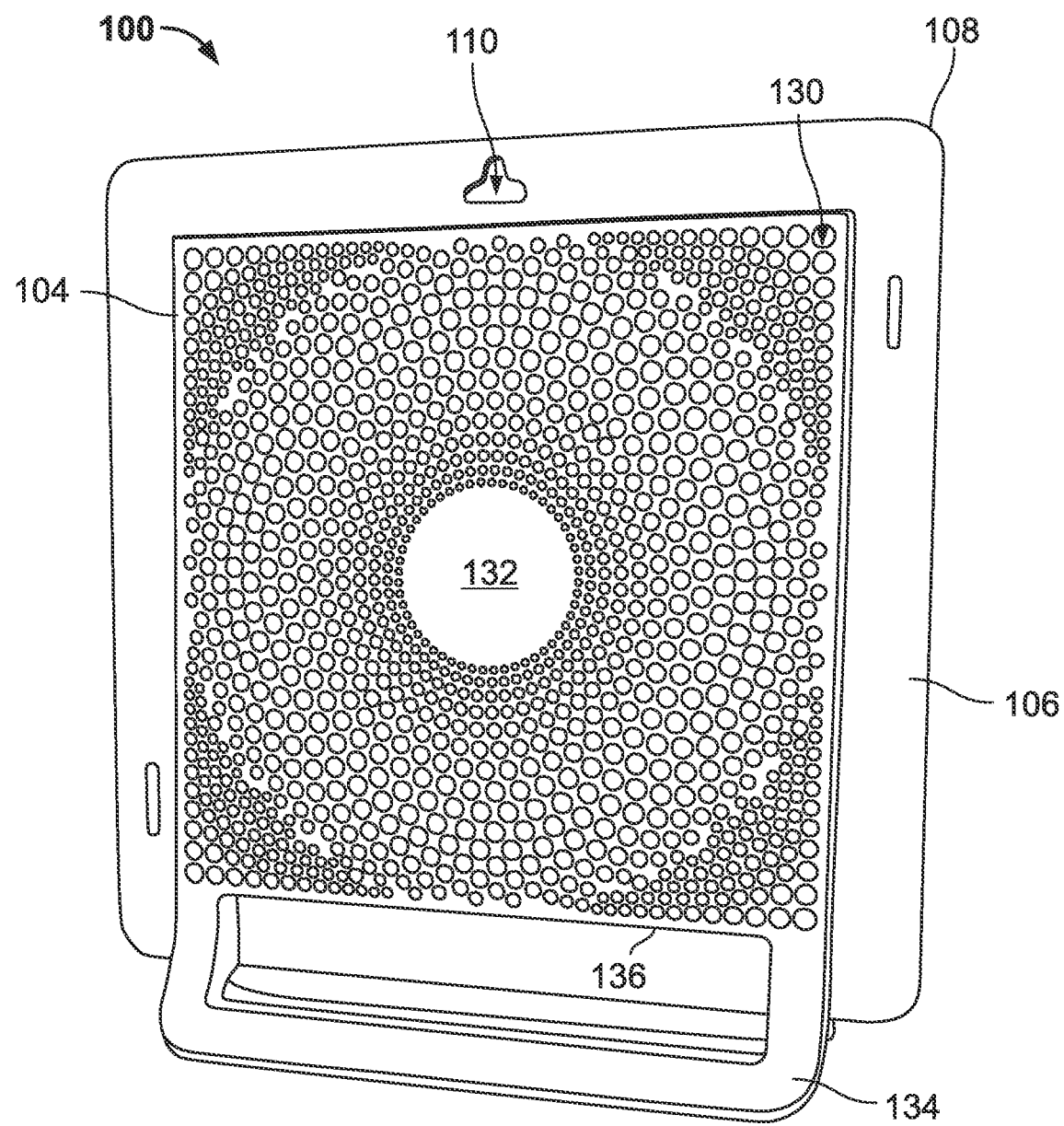
FIG. 2 is a rear isometric view of the dispenser of FIG. 1.

FIGS. 1 and 2 generally depict a dispensing device 100 for use in the emanation of a volatile material into an ambient environment and, in this particular embodiment, the passive emanation of a volatile material into an ambient environment. In one preferred embodiment, as will be further discussed herein, the dispensing device 100 is used in combination with a multi-layer substrate to emanate a pest control agent, such as a repellant or insecticide, into an ambient environment.

Still referencing FIGS. 1 and 2, the dispensing device 100 is shown to have to two opposing sides, including a front face 102 (see FIG. 1) and a rear face 104 (see FIG. 2). A central plate 106 extends between the front face 102 and the rear face 104, and a substrate (not shown) may be positioned between the front face 102 and the rear face 104, as will be further discussed herein. In these embodiments, the substrate is a reservoir for a volatile material and emanates the volatile material from the dispensing device 100 over a specified period of time.

In this embodiment, the central plate 106 is generally rectangular and includes rounded corners 108. Alternatively, in other embodiments, the dispensing device 100 and the central plate 106 may have different configurations or shapes. For example, the dispensing device 100 may be circular, ovular, triangular, square, rectangular, pentagonal, hexagonal, or any other desired geometric configuration. The central plate 106 may have an aperture 110 centrally disposed on an upper part thereof, as shown in this embodiment. The aperture 110 allows a user to hang the dispensing device 100 prior to or during use thereof. Additional apertures may be positioned around a perimeter of the central plate 106 in alternative embodiments to assist in hanging the dispensing device 100.

With particular reference to FIG. 1, the front face 102 extends from the central plate 106 and, in this embodiment, is generally rectangular with rounded corners 112. Similar to the central plate 106, the front face 102 may have alternative configurations or shapes in other embodiments. For example, in some embodiments, the front face 102 may be circular, ovular, triangular, square, rectangular, pentagonal, hexagonal, or any other desired geometric configuration. A leg 114 may extend from a bottom end 116 of the front face 102, which supports the dispensing device 100 and allows the dispensing device 100 to be placed on top of a surface (not shown) prior to or during use thereof. The front face 102 may also include a plurality of apertures 120, which allow air to enter and exit the dispensing device 100. As such, during use of the dispensing device 100, a volatile material may emanate from a substrate within the dispensing device 100 through the apertures 120.

Figure 5:
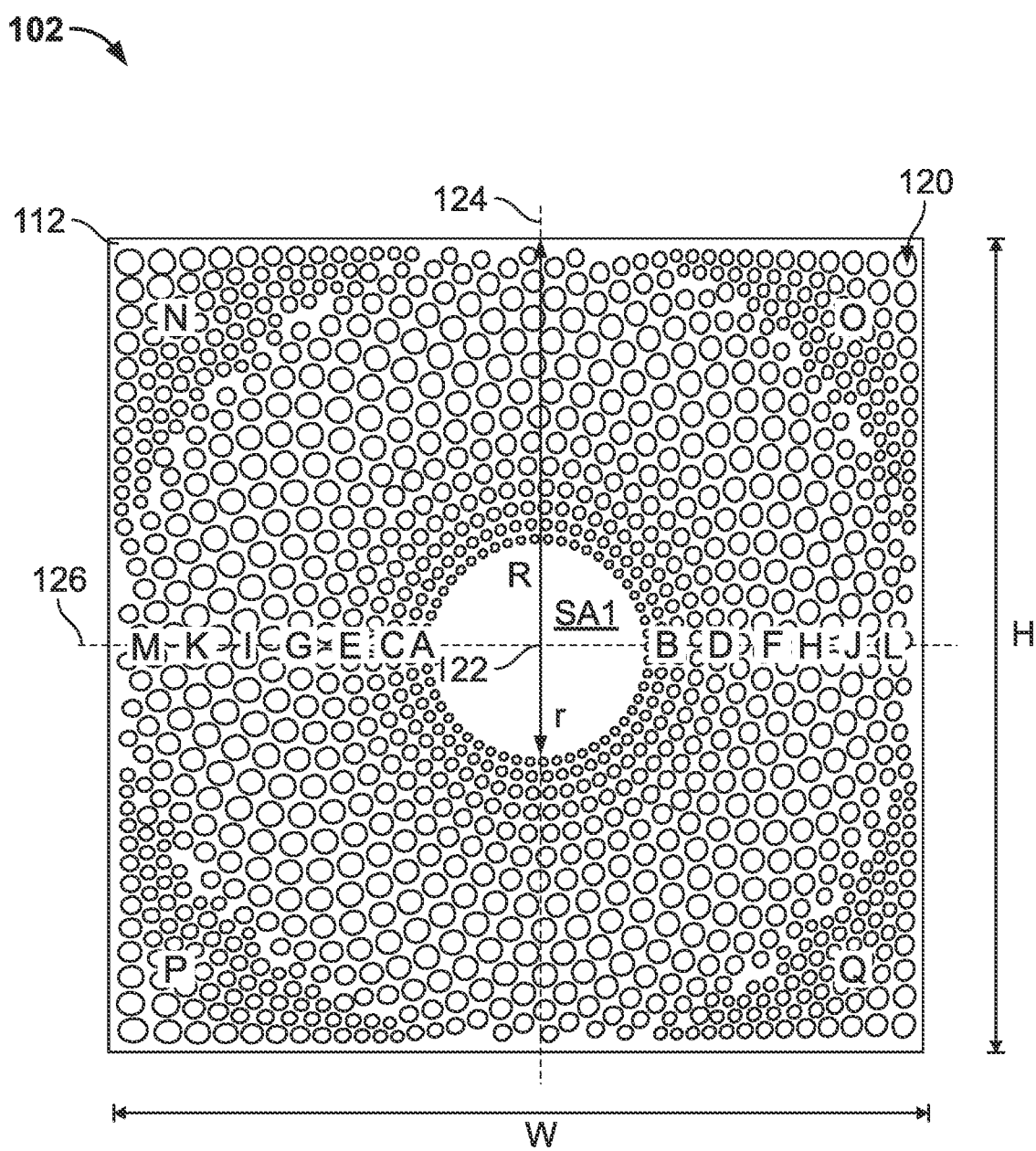
FIG. 5 is a front view of a front face of the dispenser of FIG. 1.

In particular embodiments, the front face 102, and the apertures 120 thereof, may be altered or tuned to increase or decrease the emanation rate of the volatile material from the dispensing device 100. Referring now to FIG. 5, an illustration of the front face 102 is depicted that shows the front face 102 with a height H and a width W. In some embodiments, the height H may be between about 10 centimeters and about 100 centimeters, or between about 10 cm and about 50 cm, or between about 10 cm and about 30 cm. In these embodiments, the width W may be between about 10 cm and about 100 cm, or between about 10 cm and about 50 cm, or between about 10 cm and about 30 cm. As previously discussed herein, the front face 102 may have alternative configurations and, in some embodiments, may be circular, ovular, triangular, square, rectangular, pentagonal, hexagonal, or any other desired geometric configuration. In these embodiments, the front face 102 may be dimensioned such that the front face 102 has a surface area of between about 100 $cm^2$ and about 10,000 $cm^2$, or between about 100 $cm^2$ and about 2,500 $cm^2$, or between about 100 $cm^2$ and about 900 $cm^2$.

In one aspect, as shown in FIGS. 1 and 5, the apertures 120 may be circular apertures with varying diameters. For example, with continued reference to FIGS. 1 and 5, the circular apertures 120 proximate a center 122 of the front face 102 may have the smallest relative diameter and the diameter of the apertures 120 may increase as the apertures 120 extend outwardly from the center 122 of the front face 102. In addition, as best shown in FIG. 5, the apertures 120 may be organized in a plurality of concentric rings or annular rows that extend outwardly from the center 122 of the front face 102. Further, in this particular embodiment, the diameter of the apertures 120 within each concentric circle of apertures may be uniform. However, as previously discussed herein, the diameter of the apertures 120 may generally increase as the apertures 120 extend outwardly from the center 122 or, in other words, the diameter of the apertures 120 within the first concentric circle may be the smallest and the diameter of the apertures 120 within the concentric circle farthest from the center 122 may be the largest.

In this particular embodiment, the front face 102 includes approximately 13 concentric rings or annular rows of apertures 120, i.e., annular rows A-M (see FIG. 5). However, in alternative embodiments, the front face 102 may include any number of apertures 120 to produce the desired emanation of the volatile material from the dispensing device 100. For example, in alternative embodiments, the apertures 120 may be organized into rows or columns to produce a grid configuration. In such embodiments, the front face 102 may include between 1 row and 100 rows and/or between about 1 column and 100 columns. Further, the rows and columns may individually include between 1 and 100 apertures. In other embodiments, the apertures 120 may be organized to depict particular shapes, letters, words, or images.

According to another aspect of the present disclosure, the apertures 120 within regions N-Q proximate the corners 112 of the front face 102 may have alternative configurations. For example, as best shown in FIG. 5, the apertures 120 proximate the corners 112 of the front face 102 may be in a triangular configuration. Further, the apertures 120 farthest from the corners 112 may have the smallest diameter and the apertures 120 closest to the corners 112 may have the largest diameter, in this embodiment. As such, the diameter of the apertures 120 may generally increase as the apertures 120 extend from the center 122 of the front face 102, then decrease as the apertures 120 transition between the first pattern (i.e., concentric rings or annular row of apertures) to the second pattern (i.e., triangular pattern of apertures), and then subsequently increase yet again as the apertures 120 extend to the corners 112.

In alternative embodiments, the apertures 120 may be in an inverse configuration, with the apertures 120 farthest from the corners 112 having the largest diameter and the apertures 120 closest to the corners 112 may have the smallest diameter. In yet another embodiment, the front face 102 may not include the apertures 120 within the triangular configuration. Rather, in one embodiment, the front face 112 may only include apertures 120 within concentric rings that extend to the corners 112, such that the apertures 120 only increase in diameter as they extend outwardly from the center 122 of the front face.

In alternative embodiments, the apertures 120 may be circular apertures with a uniform diameter. In other embodiments, the apertures 120 may be organized in alternative configurations, such as rows or columns, or may be arbitrary or randomly placed on the front face 102. However, in particular embodiments, the apertures 120 may be between about 35% and about 99% of the surface area of the front face 102 of the dispensing device 100. In alternative embodiments, the apertures 120 may be between about 50% and about 99% of the front face 102, or between about 75% and about 99% of the front face 102, or between about 90% and 95% of the front face 102. For example, with continued reference to FIG. 5, the front face 102 may have a total surface area (SA) defined by multiplying the width W by the height H. Further, a portion of the total surface area (SA) of the front face 102 that the apertures 120 extend throughout may be characterized by the total surface area (SA) minus the surface area (SA1), which is devoid of any of the apertures 120. In this particular embodiment, the surface area (SA1) may be calculated using the radius (r), which is defined as the distance between the center 122 of the front face 102 and an innermost edge defining one of the apertures 120 of the smallest concentric ring or annular row A, and Equation 1 below.

$$SA1 = \pi r^2 \quad \text{(Eq. 1)}$$

Additionally, the total surface area of the substrate exposed to the ambient environment (SAs) may be approximately equal to the total surface area (SA) minus the surface area (SA1), which is approximately equal to the surface area devoid of any of the apertures 120. Further, a percentage of the surface area of the substrate that is exposed may be determined by dividing the total surface area of the substrate exposed (SA$_{ES}$) by the total surface area of the substrate (SA$_s$), which in most embodiments, is equal to the total surface area (SA). The formula for determining the percentage of surface area of the substrate that is exposed is shown in Equation 2 below.

$$\% \text{ Substrate } SA \text{ Exposed} = \frac{(SA) - (SA1)}{SA_S} = \frac{SA_{ES}}{SA_S} \approx \frac{SA_{ES}}{SA} \quad \text{(Eq. 2)}$$

The concentric rings of the apertures A-M, as well as the apertures in the quadrants N-Q, may also be characterized by individual radii extending from a center of each aperture. As such, an actual measurement of the surface area that is defined by the apertures 120 may be calculated, or, the surface area devoid of any apertures may be calculated. Turning again to FIG. 5, the largest or last concentric ring of apertures M may be characterized by a radius (R), as shown in FIG. 5, which is defined by an outermost edge of one of the apertures of the largest concentric ring or annular row M. The radius (R) may also be approximately equal to half the height H of the front face 102 and/or approximately equal to half the width W of the front face 102. In these embodiments, the percentage of the surface area (SA) having the apertures within the first pattern (i.e., the concentric rings or annular rows of apertures A-M) may be calculated using Equation 3 below, and may be characterized as a first footprint or diffusion area. The percentage of the surface area having the apertures within the second pattern (i.e., regions N-Q) may be calculated using Equation 4 below, and may be characterized as a second footprint or diffusion area having four quadrants.

$$\text{SA with Apertures of First Pattern} = \pi R^2 - SA1 \quad \text{(Eq. 3)}$$

$$\text{SA with Apertures of Second Pattern} = SA - \pi R^2 - SA1 \quad \text{(Eq. 4)}$$

Additionally, the surface area of each quadrant having the alternative configuration, i.e., regions N-Q, may be calculated by dividing the surface area calculated in Equation 3 by 4.

The diameter of the apertures 120 may range between about 1 millimeter and about 25 millimeters, or between about 1 mm and about 15 mm, or between about 5 mm and about 10 mm. In alternative embodiments, the apertures 120 may be in alternative configurations. For example, the apertures 120 may be ovular, triangular, square, rectangular, pentagonal, hexagonal, or any other desired geometric shape. In such embodiments, the apertures 120 may have a surface area ranging between about 0.75 mm$^2$ and about 500 mm$^2$, or between about 0.75 mm$^2$ and about 175 mm$^2$, or between about 20 mm$^2$ and about 75 mm$^2$.

Further, as previously discussed herein, the diameter of the apertures 120 may generally increase as the apertures 120 extend outwardly from the center 122, as shown in FIG. 5 for example. As a result, the emanation rate or release rate of a volatile material from the dispensing device 100 may vary at different locations on the front face 102. For example, in this embodiment, the emanation rate may generally increase extending outwardly from the center 122 and may have a positive relationship with a size of the apertures 120. In other words, because concentric ring M includes apertures 120 having larger diameters than the apertures 120 of the concentric ring A, the emanation rate of the volatile material of the dispensing device 100 may be larger through the apertures 120 of the concentric ring M compared to the emanation rate of the volatile material through the apertures 120 of the concentric ring A. By effect, the dispensing device 100 may wick a volatile material from the center 122 and to the corners 112 of the front face 102. In alternative embodiments, the size of the apertures 120 may be altered and tuned to provide other desired airflows and emanation rates.

Figure 4:
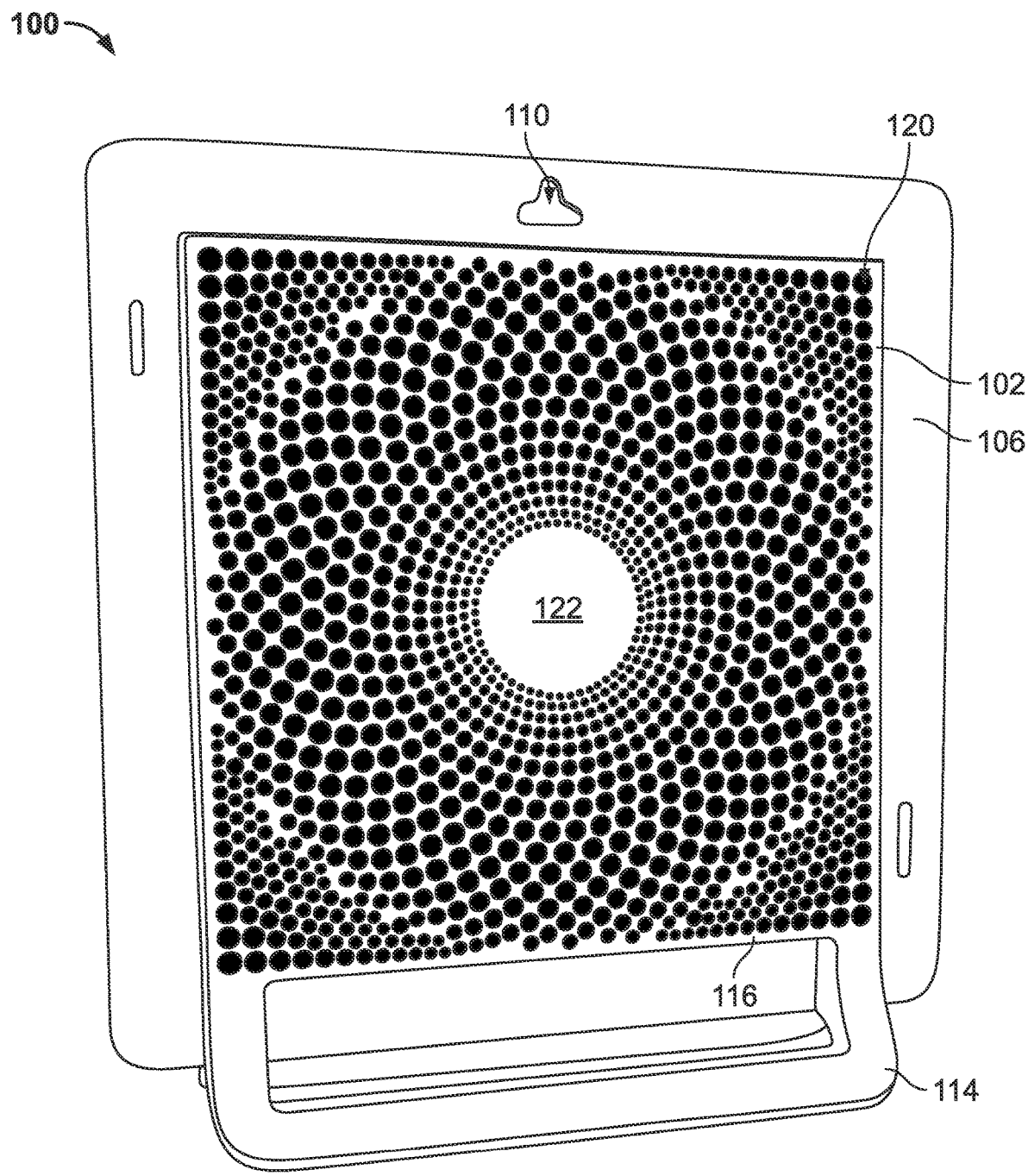
FIG. 4 is a front isometric view of a dispenser, according to another aspect of the present disclosure.

In some embodiments, the front face 102 may include between about 1 and 7,500 apertures, or between about 1 and 2,000 apertures, or between about 500 and about 1,000 apertures, or between about 700 and about 800 apertures. Still referencing FIG. 5, the apertures 120 may also have symmetry across a vertical axis 124 and/or a horizontal axis 126. Further, as shown in FIG. 4, a surface beneath the aperture 120 may be a different color than that of the front face 102.

Figure 3:
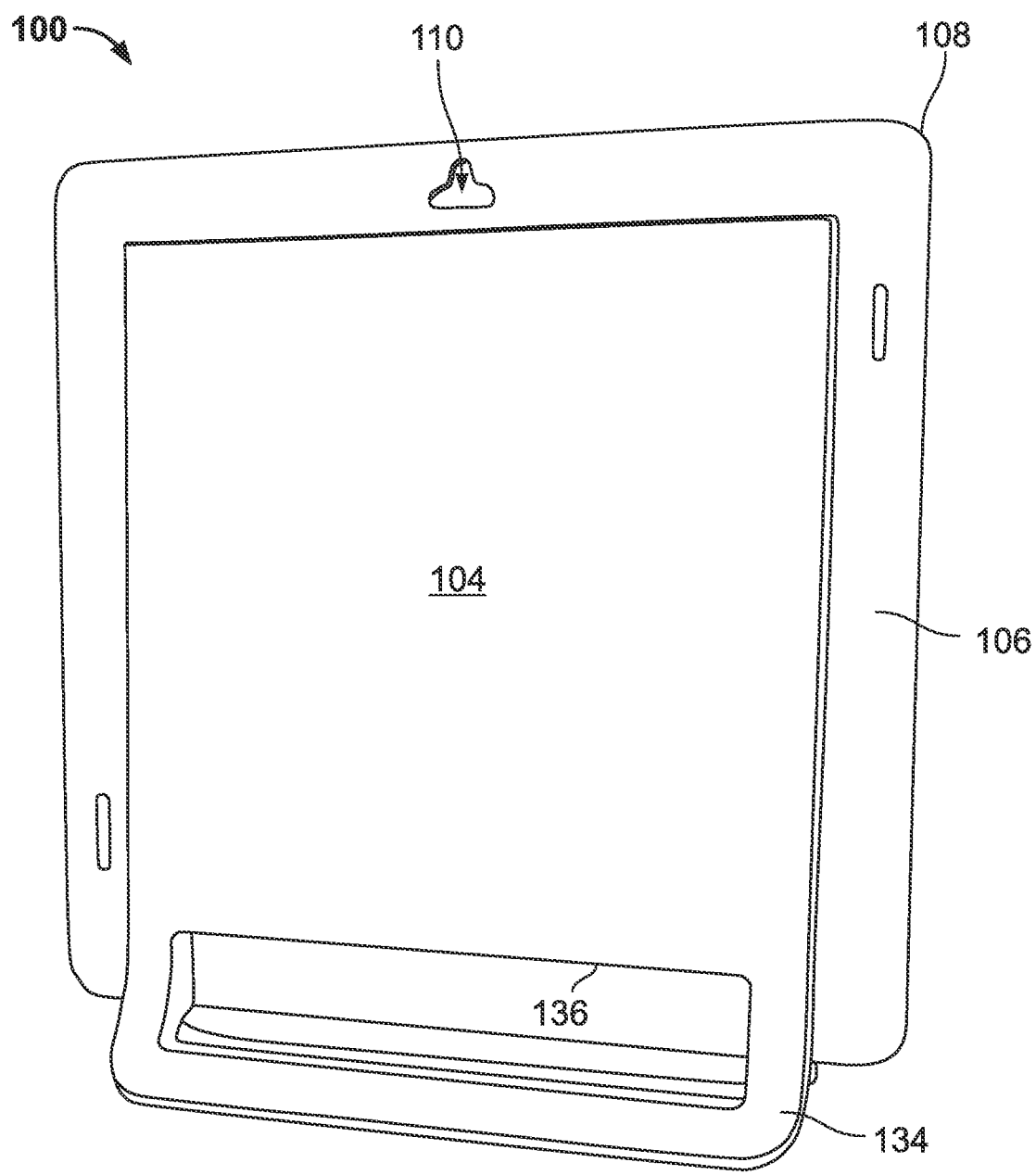
FIG. 3 is a rear isometric view of the dispenser of FIG. 1, according to a second aspect of the present disclosure.

With reference to FIG. 2, the rear face 104 of the dispensing device 100 may be similar to the front face 102 and may include a plurality of apertures 130 that extend outwardly from a center 132. However, in alternative embodiments, the rear face 104 of the dispensing device 100 may not include the apertures 130, as shown in FIG. 3. In other embodiments, the rear face 104 may be constructed independently from the front face 102 and may include apertures 130 of varying size, number, and pattern. Therefore, the aforementioned disclosure of the front face 102, and the apertures 120 thereof, equally and independently applies to the rear face 104 and the apertures 130 thereof. For example, in some embodiments, the rear face 104 may independently have a height and width between about 10 centimeters and about 100 centimeters, or between about 10 cm and about 50 cm, or between about 10 cm and about 30 cm. Additionally, the apertures 130 may be circular and may have a diameter between about 1 millimeter and about 25 millimeters, or between about 1 mm and about 15 mm, or between about 5 mm and about 10 mm, for example. Alternatively, the dispensing device 100 may not include the rear face 104 and the central plate 106 may define a rear surface of the dispensing device 100.

The dispensing device 100 may also be characterized by a thickness, which may be a distance measured between the front face 102 and the rear face 104 of the dispensing device 100. In some embodiments, the thickness of the dispensing device 100 may be between about 0.05 cm to about 10 cm.

Further, in this particular embodiment, the rear face 104 also includes a leg 134 that extends from a bottom end 136 of the rear face 104, which may support the dispensing device 100. During use, the legs 114, 136 allow the dispensing device 100 to sit or be placed on a surface (not shown).

Figure 6:
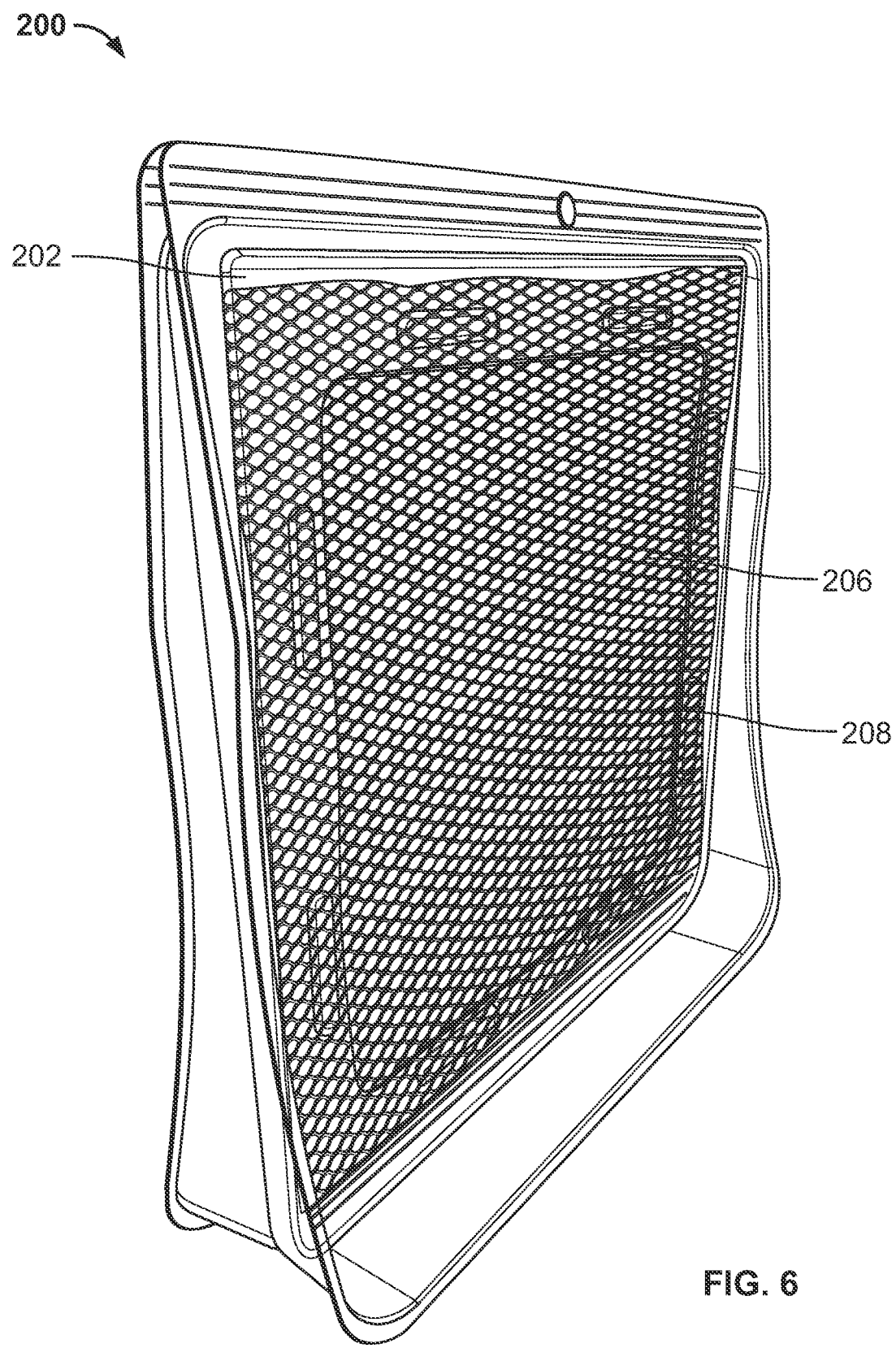
FIG. 6 is a front isometric view of a dispenser, according to yet another aspect of the present disclosure.
Figure 7:
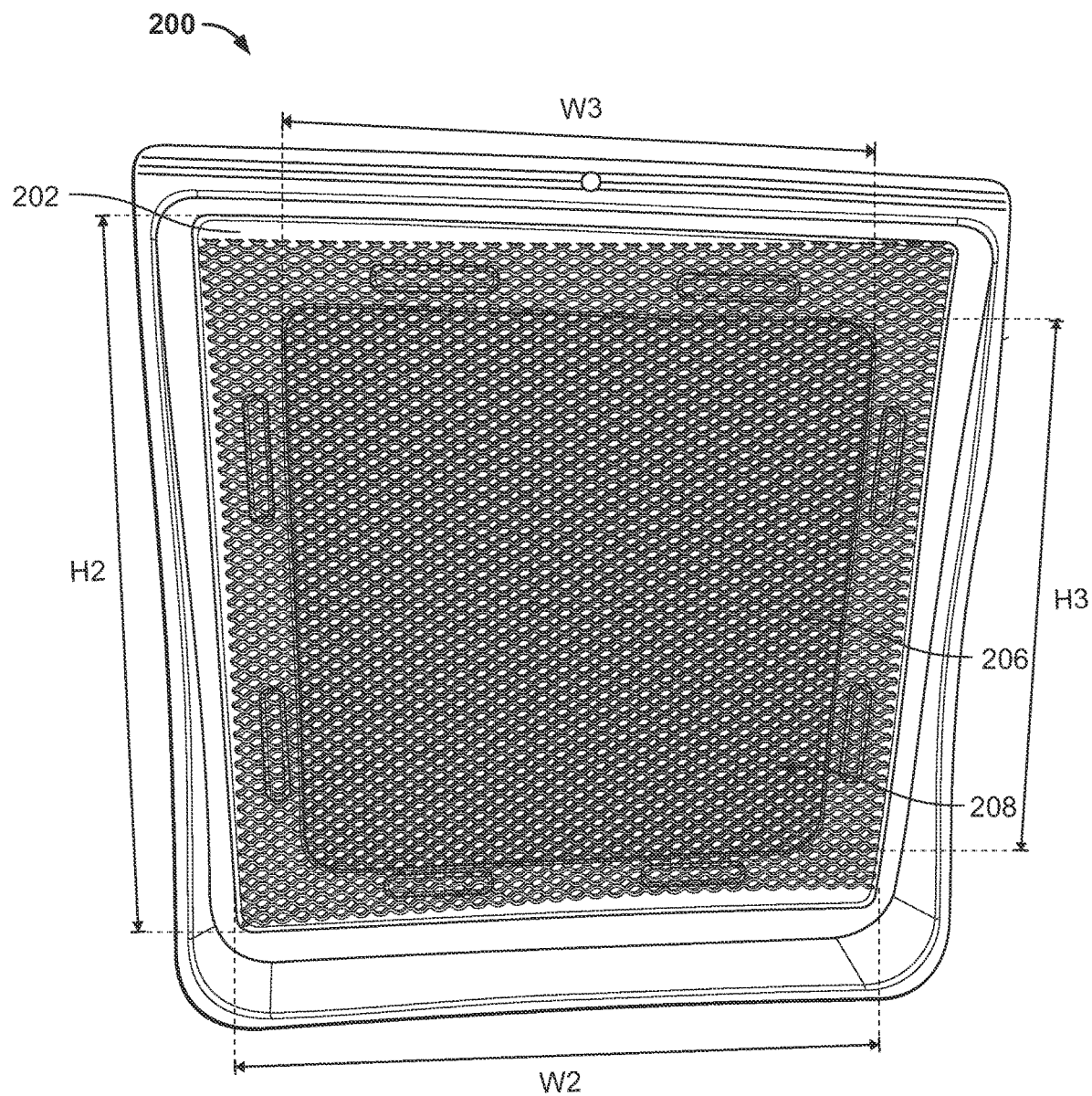
FIG. 7 is a front view of the dispenser of FIG. 6.
Figure 8:
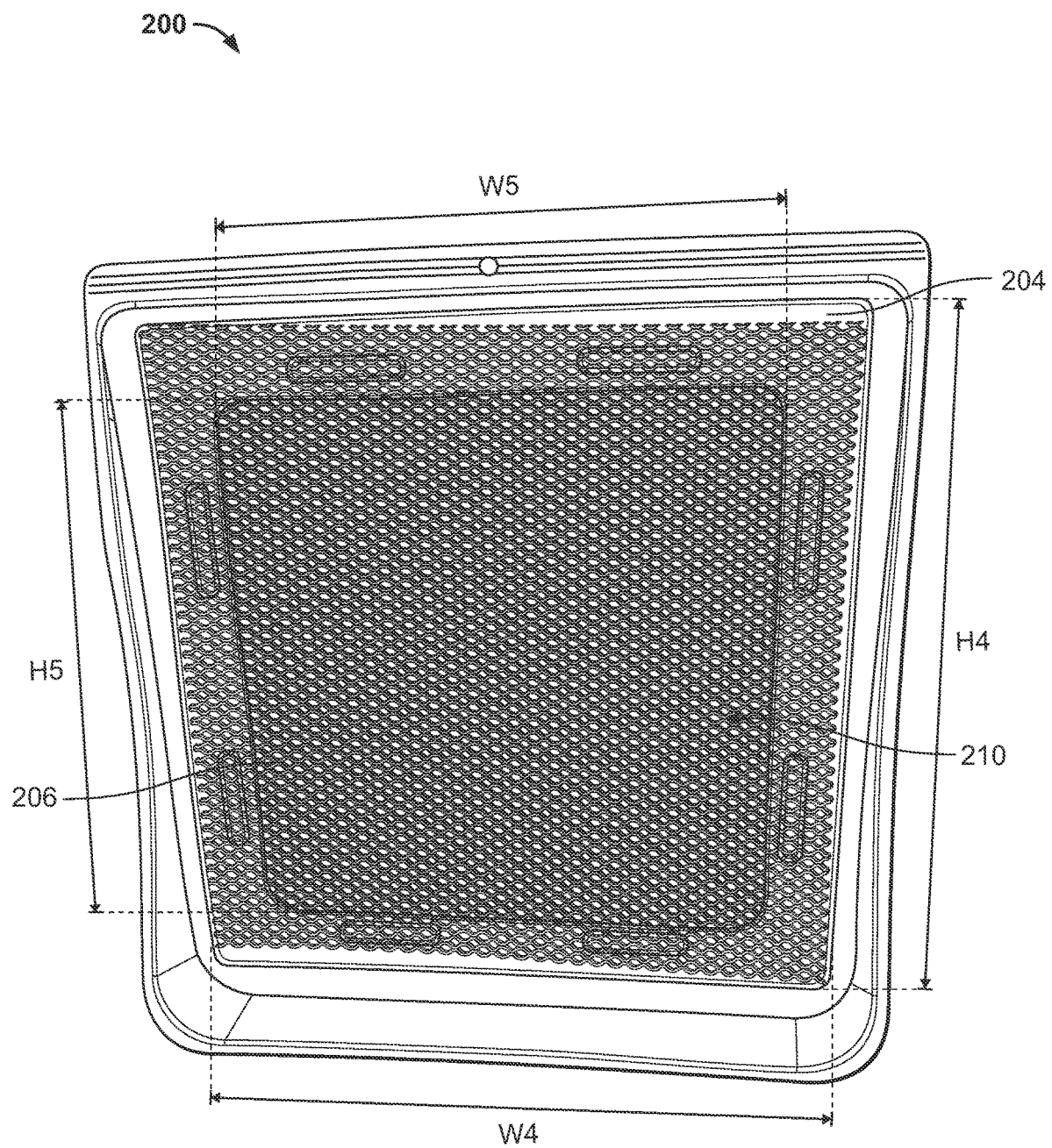
FIG. 8 is a rear view of the dispenser of FIG. 6.

FIGS. 6-8 depict another dispensing device or frame 200 for use in the emanation of a volatile material into an ambient environment, according to a second aspect of the present disclosure. Similar to the dispensing device 100, the dispensing device 200 is used in combination with a multi-layer substrate to emanate a volatile material, such as a pest control agent, a repellant, or insecticide, into an ambient environment.

The dispensing device 200 includes two opposing sides, including a front face 202 and a rear face 204, and a substrate 206 may be positioned between the front face 202 and the rear face 204. As will be discussed further, the substrate 206 is a reservoir for a volatile material and passively emanates a volatile material from the dispensing device 200 over a specified period of time.

As shown in FIGS. 6 and 7, the front face 202 includes an aperture 208 which allows airflow through the substrate 206 to provide for passive emanation of a volatile material from the substrate 206. The rear face 204 of the dispensing device 200 may be similar to the front face 202, as shown in FIG. 8, and may also include an aperture 210 that allows airflow through the substrate 206 to provide for passive emanation of a volatile material from the substrate 206. Alternatively, the rear face 204 does not include the aperture 210, and in this embodiment, the rear face 204 is closed and covers the substrate 206.

With continued reference to FIGS. 6-8, the apertures 208, 210 may be between about 50% and about 99% of the front face 202 or rear face 204, respectively. In further embodiments, the apertures 208, 210 may be between about 75% and about 99%, or between about 90% and 95% of the front face 202 or rear face 204, respectively. For example, with continued reference to FIGS. 6-8, the front face 202 may have a total surface area (SA2) defined by multiplying the width W2 by the height H2 and the rear face 204 may have a total surface area (SA3) defined by multiplying the width W3 by the height H3. As such, the apertures 208, 210 may expose between about 50% and about 99%, or between about 75% and about 99%, or between about 90% and 95% of the substrate 206 to the ambient environment. Thus, similar to the dispensing device 100, the front face 202 and the rear face 204, and the apertures 208, 210 thereof, may be sized to increase or decrease the emanation rate of the volatile material from the dispensing device 200.

Referring now to FIGS. 7 and 8, the heights H2, H4 and the widths W2, W4 may be similar in dimension to the height H and the width W of the dispensing device 100. More particularly, the heights H2, H3 and the widths W2, W3 may be individually between about 10 centimeters and about 100 centimeters, or between about 10 cm and about 50 cm, or between about 10 cm and about 30 cm. In these embodiments, the front face 202 and/or the rear face 204 may be dimensioned such that the front face 202, or the rear face 204, has a surface area of between about 100 cm$^2$ and about 10,000 cm$^2$, or between about 100 cm$^2$ and about 2,500 cm$^2$, or between about 100 cm$^2$ and about 900 cm$^2$.

The front face 202 and the rear face 204, and the apertures 208, 210 thereof, may be altered or tuned to increase or decrease the emanation rate of the volatile material form the dispensing device 200. With reference to FIGS. 7 and 8, the apertures 208, 210 may be defined by a height H3, H5 and a width W3, W5, respectively, and the surface area of the exposed substrate (SA$_{ES}$) may be calculated by multiplying the height H3, H5 by the width W3, W5, in this embodiment. Thus, the percentage of substrate surface area exposed to the ambient environment can be calculate by dividing the surface area of the exposed substrate (SA$_{ES}$) by the total surface area of the substrate (SA$_s$), which in most embodiments, is equal to the total surface area (SA) of the front face 202 or the rear face 204. The total surface area (SA) of the front face 202 or the rear face 204 can be calculated using the height H2, H4 and width W2, W4 dimensions. In this embodiment, the total surface area (SA) of the front face 202 or the rear face 204 can be calculated by multiplying the height H2, H4 of the front face 202 or rear face 204 by the width W2, W4 thereof. The formula for determining the percentage of surface area of the substrate that is exposed to an ambient environment is shown in Equation 5 below.

$$\% \text{ Substrate } SA \text{ Exposed} = \frac{SA_{ES}}{SA_S} \approx \frac{SA_{ES}}{SA} \quad \text{(Eq. 5)}$$

Similar to the dispensing device 100, the front face 202 and the rear face 204, and the apertures 208, 210 thereof, may be altered or tuned to increase or decrease the emanation rate of the volatile material from the dispensing device 200. As previously noted herein, the apertures 208, 210 may be between about between about 35% and about 99% of the surface area of the front face 202 or rear face 204 of the dispensing device 200. In alternative embodiments, the apertures 208, 210 may be between about 50% and about 99% of the front face 202 or rear face 204; or between about 75% and about 99% of the front face 202 or rear face 204; or between about 90% and 95% of the front face 202 or rear face 204. As a result, the percentage of the surface area of the substrate exposed ($SA_{ES}$) may be between about 50% and about 99%, or between about 75% and about 99%, or between about 90% and about 95%.

Substrates

Figure 9:
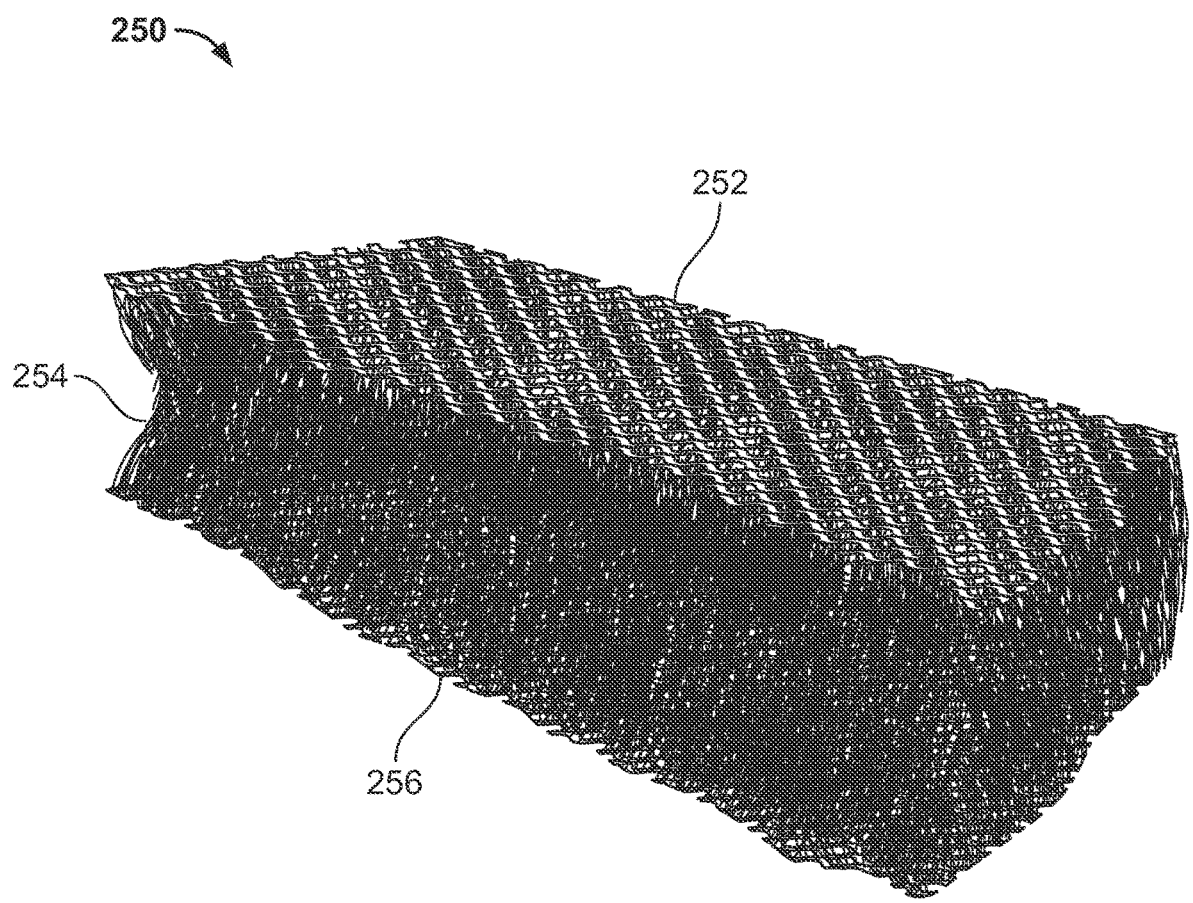
FIG. 9 is a side view of a substrate for use with the dispensers of FIGS. 1 and 6.

FIG. 9 illustrates a portion of a substrate 250 that may be used in combination with the dispensing device 100 or the dispensing device 200. As will be further discussed herein, the substrate 250 may be constructed from one or more layers and may be a 3-dimensional fabric material used for the passive emanation of an active agent of a volatile material. In one embodiment, the structure of the substrate 250 may include a plurality of woven and non-woven layers that may be layered to produce the substrate 250. For example, as shown in FIG. 9, the substrate 250 may include a first layer 252, a second layer 254, and a third layer 256. However, according to alternative aspects of the present disclosure, the substrate 250 may include additional layers or, alternatively, only a first and second layer, such as only the first layer 252 and the second layer 254.

The configuration of the substrate 250, and the layers thereof, produces a substrate 250 with a high surface area per projected volume. More particularly, the first layer 252 and/or the third layer 256 may provide an optimal layer for wicking and subsequently emitting a volatile material or active agent using a plurality of pores that allow air to flow through the substrate 250 and the layers thereof; and the second layer 254 may provide an optimal layer for storing a volatile material or active agent over a prolonged period of time.

According to aspects of the present disclosure, the physical properties of the layers of the substrate 250 may be optimized to achieve a desired wicking, saturation, and rate of evaporation. More particularly, a thickness, porosity, weave pattern, material, and/or space density of the layers of the substrate 250 may be optimized to achieve a desired wicking, saturation, and rate of evaporation of an active agent from the substrate 250, for example. Further, a thickness, porosity, weave pattern, material, and/or space density of the layers of the substrate 250 may be optimized to achieve a desired product lifetime or emanation life time, such as a length of time during which the substrate 250 constantly emanates an active agent therefrom. As will be further discussed herein, the substrate 250, and the properties thereof, may be tuned such that the substrate 250 passively and consistently emanates an active agent, such as transfluthrin, over a period of time, such as one week, ten days, two weeks, three weeks or four weeks, six weeks or eight weeks, most preferably.

As discussed above, the substrate 250 may include the first layer 252, the second layer 254, and the third layer 256. Further, in particular embodiments, the first layer 252, the second layer 254, and the third layer 256 may have individual properties; however, in some embodiments, the first layer 252, the second layer 254, and the third layer 256 may be constructed from the same material, may be interwoven, and may contain continuous fibers therebetween. For example, the first layer 252 and the third layer 256 may be woven layers and the second layer 254 may be a non-woven layer extending therebetween. Further, the fibers of the second layer 254 may connect the fibers of the first layer 252 and the third layer 256.

First Layer of the Substrate

The first layer 252 may be formed using one or more materials to provide sufficient wicking, saturation, and rate of evaporation. For example, in particular embodiments, the first layer 252 may be the top layer of the substrate 250 and may be a woven fibrous material constructed from a cotton, polyester, or nylon based material. In these embodiments, the first layer 252 may have a pore size, a weave pattern, a thickness, a porosity, and a density.

The pore size of the first layer 252 may range between about 0.5 millimeters and about 20 millimeters, or between about 1 mm and about 10 mm, or between about 1 mm and about 5 mm, or between about 2 mm and about 5 mm, or any pore size between the aforementioned values to provide the desired emanation rate of a volatile material from the substrate 250, as will be further discussed herein. For example, if a dispensing device 100, 200 with a rapid emanation rate is desired, the pore size of the first layer 252 may be substantially higher than a pore size of a first layer 252 of a substrate 250 for a dispensing device 100, 200 where a slow emanation rate is desired.

Additionally, the pore size of the first layer 252 may be dependent on the construction of the dispensing device 100, 200 to be used in combination with the substrate 250. More particularly, the pore size of the first layer 252 and the total surface area of the substrate 250 that is exposed to the ambient environment, by way of the configuration of the apertures of the dispensing devices 100, 200, each affect the emanation rate of the volatile material or active agent from the substrate 250. Therefore, when designing the substrate 250, the first layer 252, and the properties thereof (i.e., the pore size), may be tuned in combination with the dispensing device to be used therewith.

Figure 10:
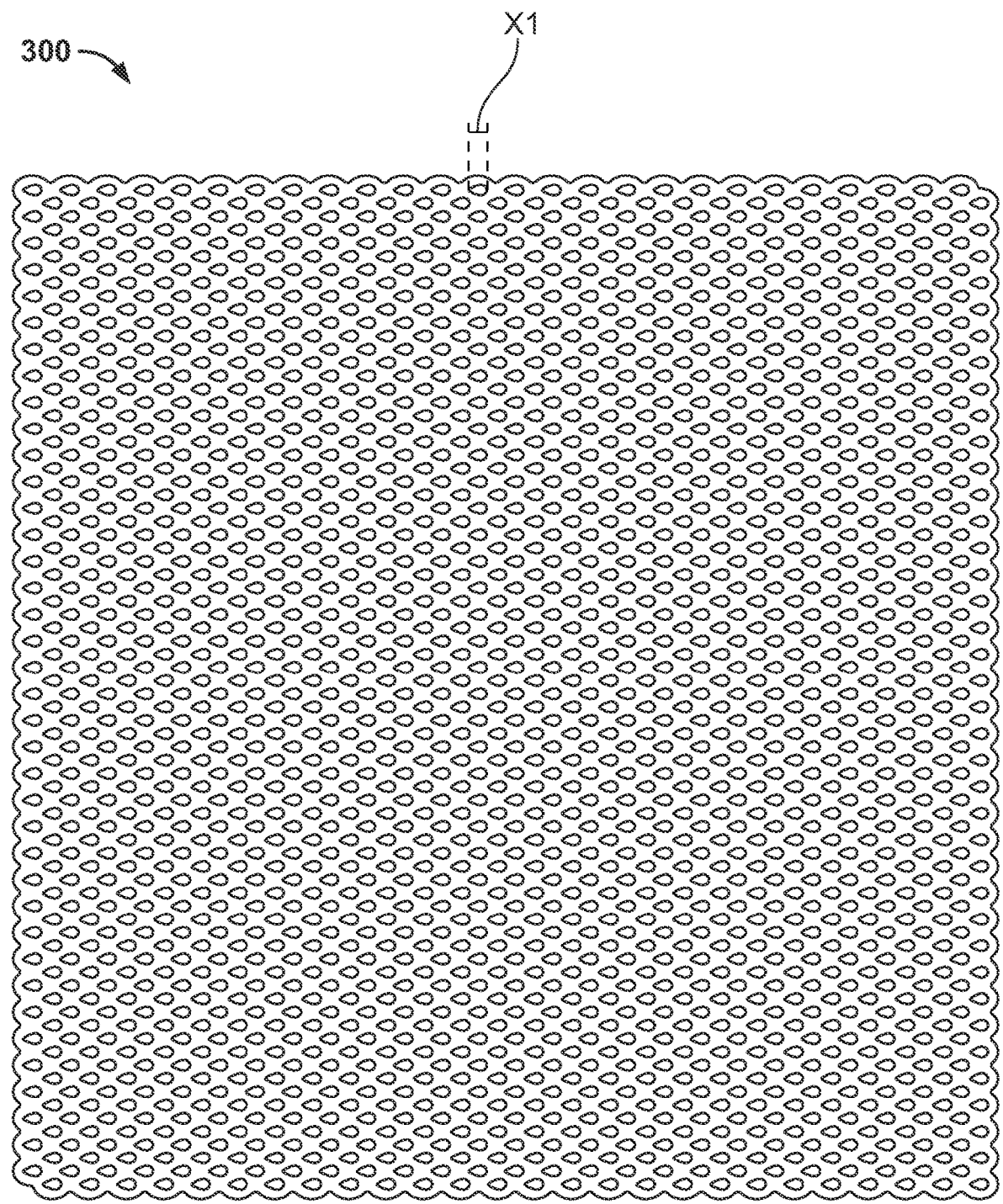
FIG. 10 is a top plan view of a portion of another substrate for use with the dispensers of FIGS. 1 and 6.
Figure 11:
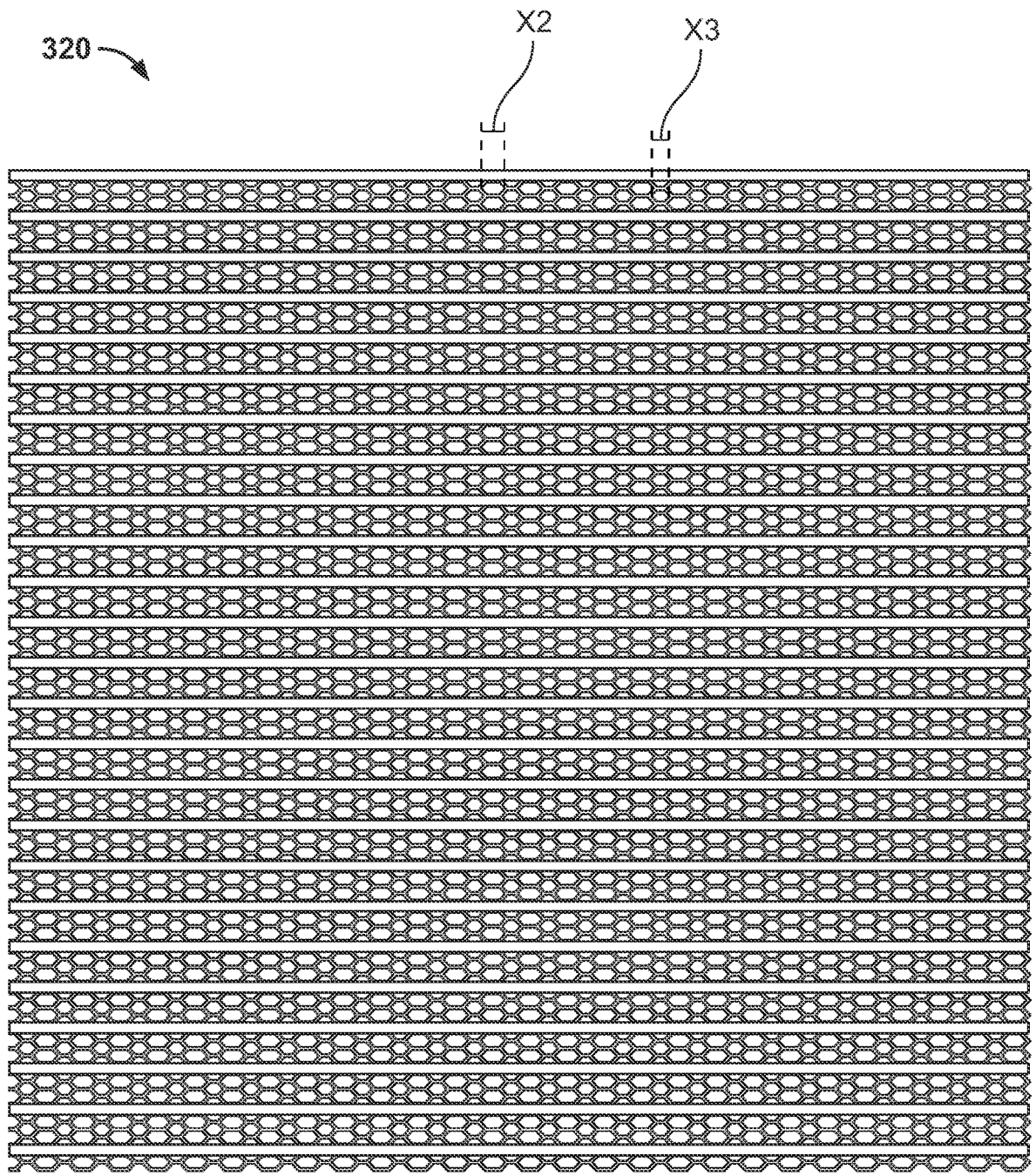
FIG. 11 is a top plan view of a portion of yet another substrate for use with the dispensers of FIGS. 1 and 6.

To provide non-limiting examples, FIG. 10 depicts a substrate 300 having a pore size X1 of about 3 mm and FIG. 11 depicts a substrate 320 having a pore size X2 of about 5 mm, both of which may be utilized for the first layer 252 of the substrate 250 or the third layer 256 of the substrate 250. Further, in some embodiments, the top layer 252 may also include multiple pore sizes. For example, with reference to FIG. 11, the substrate 320 may include a pore size X2 and a pore size X3.

As noted above, the weave pattern, thickness, and density of the first layer 252 may also be optimized to produce a desired emanation rate. For example, in the embodiment where the first layer 252 is a woven material, the weave pattern of the first layer 252 may be adjusted to control the rate of wicking. In one preferred embodiment, the optimal weave pattern creates a preferred balance between the release rate of the volatile material therein and an internal surface area, which acts as a reservoir for the volatile material therein.

As will be further discussed herein, the first layer 252 may be constructed from textiles produced by Gehring-Tricot Warp Knit Fabrics located in St. Johnsonville, New York and Dolgeville, New York, such as the D3® Spacer fabrics. Specific, non-limiting, examples of materials or textiles that may be used to construct the first layer 252 include the following fabrics produced by the Gehring-Tricot Corporation: Gehring Green, SHR 714F, SHR 796F, SHR 918, SHR 891, SHR 896, SHR 701/6, SHR 711/6, SHR 878, SHR 863 SHR 884, SHR 895, SHR 844, SHR 860/1, SHR 724/5, and SHR 702/1. The aforementioned fabrics will be discussed in further detail in the examples herein.

Examples of materials that are satisfactory for forming the first layer 252 include textile based materials, such as cotton, polyester, nylon, rayon, or a combination thereof. In further embodiments, the first layer 252 may be formed from a plant-based material, such as hemp fibers.

The thickness of the first layer 252 may also be optimized for the particular use for the substrate 250. As will be further discussed herein, the thickness of the first layer 252 is positively correlated to the release rate; thus, if a higher release rate or emanation rate is desired, a material with a larger thickness may be used for the first layer 252. In particular embodiments, a thickness of the first layer 252 may range between about 0.1 millimeters and about 6 millimeters, or between about 0.3 mm and about 5 mm, or between about 0.3 and about 3 mm, or between about 1 mm and about 2.5 mm, or between about 1 mm and 2 mm.

Second Layer of the Substrate

The second layer 254 may also be formed using one or more materials to provide sufficient wicking, saturation, and rate of evaporation. For example, in particular embodiments, the second layer 254 may be an intermediate, spacer layer positioned between the first layer 252 and the third layer 256. In these embodiments, the second layer 254 may be a fibrous, non-woven material, such as a cotton, polyester, or nylon based material. Further, in these embodiments, the second layer 254 may have a thickness and may be altered to tune the density, thickness, and surface area to volume ratio of the substrate 250.

As noted above, the thickness and density of the second layer 254 may also be optimized to produce a desired emanation rate. More particularly, in certain embodiments, the spacer thickness and the density of the second layer 254 may be varied to control the degree of saturation of the substrate 250 (i.e., the amount of volatile material capable of being stored within the substrate 250) and, as a result, the duration of emanation of the volatile material from the substrate 250. In these embodiments, the second layer 254 may act as a reservoir for the volatile material having the active agent. As such, the density of the second layer 254 may be increased or decreased to control the degree of saturation of the volatile material or active agent. For example, if a higher degree of saturation is desired, the density of the fibers of the second layer 254 can be increased to increase the surface density of the substrate 250. As will be further discussed herein, the second layer 254 may be altered by increasing or decreasing the fibers therein, such that a surface density of the substrate 250 ranges between about 75 grams per square meter (g/m$^2$) and about 500 grams per square meter, or between about 150 g/m$^2$ and about 400 g/m$^2$, or between about 150 g/m$^2$ and about 350 g/m$^2$, or between about 200 g/m$^2$ and about 320 g/m$^2$, or between about 250 g/m$^2$ and about 300 g/m$^2$, or about 280 g/m$^2$.

In addition to altering the density of the second layer 254, the thickness of the second layer 254 may be altered. The thickness of the second layer 254 may be generally defined as the distance between the first layer 252 and the second layer 254, i.e., the distance through which the fibers of the second layer 254 extend. In particular embodiments, a thickness of the second layer 254 may range between about 0.1 millimeters and about 6 millimeters, or between about 0.5 mm and about 5 mm, or between about 0.5 mm and about 5 mm, or between about 1 mm and about 4 mm, or between about 2 mm and 3 mm, or between about 0.1 mm and about 0.3 mm.

Examples of materials, or fibers, which are satisfactory for forming the second layer 254 include textile based materials, such as cotton, polyester, nylon, rayon, or a combination thereof. In further embodiments, the first layer 252 may be formed from a plant-based material, such as hemp fibers.

Third Layer of the Substrate

The third layer 256 may be formed using one or more materials to provide sufficient wicking, saturation, and rate of evaporation. In particular embodiments, the third layer 256 may be the bottom layer of the substrate 250 and may be a woven fibrous material constructed from a cotton, polyester, or nylon based material. In these embodiments, the third layer 256 may have a pore size, a weave pattern, a thickness, a porosity, and a density.

The pore size of the third layer 256 may range between about 0 millimeters and about 20 millimeters, or between about 1 mm and about 10 mm, or between about 1 mm and about 5 mm, or between about 2 mm to about 5 mm, or any pore size between the aforementioned values to provide the desired emanation rate of a volatile material from the substrate 250, as will be further discussed herein. For example, if a dispensing device 100, 200 with a rapid emanation rate is desired, the pore size of the third layer 256 may be substantially higher than a pore size of a third layer 256 of a substrate 250 for a dispensing device 100, 200 where a slow emanation rate is desired. Additionally, the pore size of the third layer 256 may be dependent on the construction of the dispensing device 100, 200 to be used in combination with the substrate 250. For example, in one embodiment, the third layer 256 may be proximate the rear face 104 of the dispensing device 100 when placed therein. As such, in these embodiments, the pore size of the third layer 256 may be between about 1 mm and about 5 mm to allow for emanation of an active agent of a volatile material within the substrate 250 when the rear face 104 includes the apertures 130, such as that shown in FIG. 2. However, in an alternative embodiment, the pore size of the third layer 256 may be 0 mm when the rear face 104 does not include the apertures 130, such as that shown in FIG. 3.

As noted above, the weave pattern, thickness, and density of the third layer 256 may also be optimized to produce a desired emanation rate. For example, in the embodiment where the third layer 256 is a woven material, the weave pattern of the third layer 256 may be adjusted to control the rate of wicking.

As will be further discussed herein, the third layer 256, similar to the first layer 252, may be constructed from textiles produced by Gehring-Tricot Warp Knit Fabrics located in St. Johnsonville, New York and Dolgeville, New York, such as the D3® Spacer fabrics. Specific, non-limiting, examples of materials or textiles that may be used to construct the first layer 252 include the following fabrics produced by the Gehring-Tricot Corporation: Gehring Green, SHR 714F, SHR 796F, SHR 918, SHR 891, SHR 896, SHR 701/6, SHR 711/6, SHR 878, SHR 863 SHR 884, SHR 895, SHR 844, SHR 860/1, SHR 724/5, and SHR 702/1. The aforementioned fabrics will be discussed in further detail in the examples herein.

Generally, examples of materials that are satisfactory for forming the third layer 256 include textile based materials, such as cotton, polyester, nylon, rayon, or a combination thereof. In further embodiments, the third layer 256 may be formed from a plant-based material, such as hemp fibers.

The thickness of the third layer 256 may also be optimized for the particular use for the substrate 250. As will be further discussed herein, the thickness of the third layer 256 is positively correlated to the release rate; thus, if a higher release rate or emanation rate is desired, a material with a larger thickness may be used for the third layer 256. In particular embodiments, a thickness of the third layer 256 may range between about 0.1 millimeters and about 6 millimeters, or between about 0.3 mm and about 5 mm, or between about 0.3 and about 3 mm, or between about 1 mm and about 2.5 mm, or between about 1 mm and 2 mm.

The aforementioned layers of the substrate 250 may also be individually altered to create a substrate having an optimal density, thickness, wicking rate, release or emanation rate, or saturation.

In particular embodiments, the layers of the substrate 250, and the properties thereof, may be altered to provide a substrate 250 having a saturation ranging between about 1 milligram (mg) and about 10,000 mg, or between about 1 mg and about 5,000 mg, or between about 1 mg and about 3,000 mg of volatile material, or between about 50 mg and about 100 mg of volatile material, or between about 1,500 mg and about 2,300 mg of volatile material, or between about 100 mg and about 700 mg, or between about 150 mg and about 400 mg, or between about 150 mg and about 300 mg of volatile material. In related embodiments, the layers of the substrate 250, and the properties thereof, may be altered to provide a substrate 250 having a saturation ranging between about 0.005 mg/cm$^2$ and about 55 mg/cm$^2$, or between about 0.005 mg/cm$^2$ and about 30 mg/cm$^2$, or between about 0.2 mg/cm$^2$ and about 0.4 mg/cm$^2$, or between about 6.5 mg/cm$^2$ and about 10 mg/cm$^2$, or between about 0.4 mg/cm$^2$ and about 3 mg/cm$^2$, or between about 0.6 mg/cm$^2$ and about 1.7 mg/cm$^2$, or between about 0.6 mg/cm$^2$ and about 1.3 mg/cm$^2$.

In some embodiments, the layers of the substrate 250, and the properties thereof, may be altered to provide a substrate 250 having a thickness ranging between about 0.1 millimeters and about 6 millimeters, or between about 1 and about 4 mm, or between about 1.5 mm and about 3 mm, or between about 1.7 mm and about 2.5 mm, or any thickness between the aforementioned values to provide the desired emanation rate of a volatile material from the substrate 250, as will be further discussed herein.

In further embodiments, the layers of the substrate 250, and the properties thereof, may be altered to provide a substrate 250 having a surface density ranging between about 75 grams per square meter (g/m$^2$) and about 500 grams per square meter, or between about 150 g/m$^2$ and about 400 g/m$^2$, or between about 150 g/m$^2$ and about 350 g/m$^2$, or between about 200 g/m$^2$ and about 320 g/m$^2$, or between about 250 g/m$^2$ and about 300 g/m$^2$, or about 250 g/m$^2$, or about 280 g/m$^2$, or any density between the aforementioned values to provide the desired emanation rate of a volatile material from the substrate 250, as will be further discussed herein. In a preferred embodiment, the substrate 250 has a density ranging between about 40 g/m$^2$ and 70 g/m$^2$.

Figure 12A:
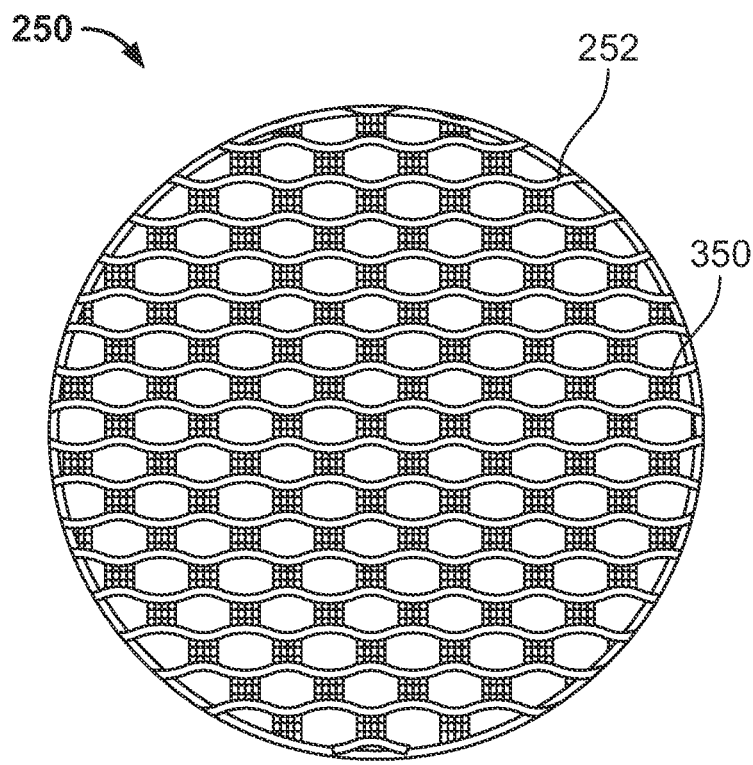
FIG. 12A is a top plan view of a portion of the substrate of FIG. 9 in a first state.
Figure 12B:
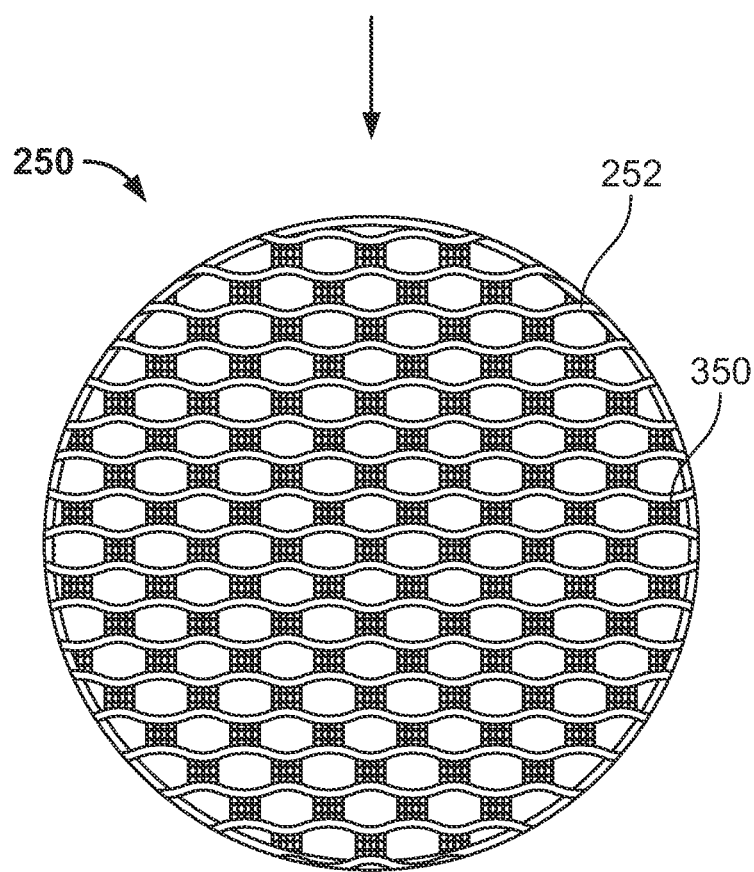
FIG. 12B is a top plan view of a portion of the substrate of FIG. 9 in a second state.

In some embodiments, the substrate 250 may also include a use-up cue that indicates to a user that the dispensing device 100, 200 has volatized all or nearly all of the volatile material therefrom. For example, as shown in FIGS. 12A and 12B, the first layer 252 of the substrate 250 may include a bright colored textile fiber and a dark colored textile fiber, which provide contrast that may be used as a visual cue or dose cue that shows the presence of a volatile material on the substrate 250. For example, when the substrate 250 does not include a volatile material, bright colored textile fibers 350 provide a visual cue or appearance, as shown in FIG. 12A, and when the substrate 250 is dosed with a volatile material, the bright colored textile fibers are less apparent, thereby indicating that a volatile material is present thereon or therein, as shown in FIG. 12B.

The dispensing device 100, 200 and the substrate 250 therein may include any suitable volatile material. In some embodiments, the volatile material may include an active agent, such as a fragrance, an insecticide, a deodorizer, a fungicide, a bacteriocide, a sanitizer, a pet barrier, or other active volatile or other compound disposed within a carrier liquid, e.g., an oil-based, organic based, and/or water based carrier or solvent, a deodorizing liquid, or the like, and/or combinations thereof. In particular embodiments, the dispensing device 100, 200 includes an insect control agent, an insect repellant, or an insecticide. Examples of possible insecticides that may be suitable in the volatile material include pyrethroids such as metafluthrin, transfluthrin, tefluthrin, and vaporthrin, or natural actives (geraniol, etc.) or a blend of these insecticides.

Additional examples of an active agent that may be used in the volatile material may include RAID®, Pyrel®, POLIL®, AUTAN®, OUST™ or GLADE®, sold by S. C. Johnson & Son, Inc., of Racine, Wisconsin. The volatile material may also comprise other actives, such as sanitizers, air and/or fabric fresheners, cleaners, odor eliminators, mold or mildew inhibitors, insect repellents, and the like, or others that have aromatherapeutic properties. The volatile material alternatively comprises any fluid know to those skilled in the art that can be dispensed from a container, such as those suitable for dispersal in the form of particles or droplets suspended within a gas and/or propelled by means of a propellant.

In some embodiments, the active agent, such as transfluthrin, may be present in the volatile material in an amount between about 5 wt. % and about 95 wt. %, between about 60 wt. % and about 90 wt. %, or between about 70 wt. % and about 85 wt. %, or even more specifically, between about 75 wt. % and about 85 wt. %. In a particular embodiment, the insect control agent may be about 80 wt. % of the volatile material and, in a preferred embodiment, transfluthrin may be about 80 wt. % of the volatile material.

The volatile material may also comprise liquids, solids, or vapors. In one aspect, the volatile material may include one or more solvents, such as an organic or aqueous solution, in which the insect control agent may be dissolved. For example, in certain aspects, the active agent may be in a solid state at room temperature (23° C.), and a solvent may be added to the active agent in order to provide and keep the volatile material in a liquid state, thus allowing the volatile material to spread, be coated on, and positioned within the substrate 250. In further embodiments, the volatile material may include a fragrance. However, in other embodiments, the volatile material may not be mixed with any other components and may consist solely of the active agent.

The dispensing device 100, 200 can provide delivery of the volatile material from the dispensing device 100, 200 at an initial delivery rate that is measured within one hour of exposing the volatile material and the dispensing device 100, 200 to the atmosphere. The dispensing device 100, 200 can provide delivery of the volatile material across, or from, the first layer 252 at a subsequent delivery rate that is measured at a fixed time after exposing the volatile material and the substrate 250 of the dispensing device 100, 200 to the atmosphere. The fixed time can be any length of time over which the vapor-dispensing device is desired to provide delivery of the volatile composition. For example, the fixed time can be six hours, twelve hours, one day, two days, three days, four days, five days, six days, one week, ten days, two weeks, fifteen days, twenty days, three weeks, twenty-five days, four weeks, thirty days, five weeks, forty days, six weeks, forty-five days, seven weeks, fifty days, fifty-five days, eight weeks, ten weeks, twelve weeks, fifteen weeks, twenty weeks, twenty-five weeks, thirty weeks, one year, and the like. More particularly, the dispensing device 100, 200 and the substrate 250 and, more particularly, the properties thereof, may be chosen to provide a dispensing device 100, 200 that emanates a volatile material over a specified and desired amount of time at a generally constant rate.

As described herein, the substrate 250, or the dispensing devices 100, 200, may be characterized as having a constant emanation rate, or a steady state emanation rate, if the emanation or release of the volatile material or active agent may be graphed or fitted with a linear regression line with a correlation of determination, i.e., an $R^2$ value, of greater than 0.8, or greater than 0.85, or greater than 0.90, or greater than 0.95, or greater than 0.98.

In certain aspects, the particular surface area and formulation concentration of the dispensing device 100, 200 may be designed to constantly emanate between about 0.1 mg/day and about 10 mg/day of the active agent or the volatile material, between about 1 mg/day and about 10 mg/day, between about 1 mg/day and about 7 mg/day, between about 1 mg/day and about 5 mg/day of the active agent or the volatile material, or between about 1.5 mg/day and about 4 mg/day of the active agent or the volatile material, or between about 1.5 mg/day and about 2 mg/day of the active agent or the volatile material. In further embodiments, the dispensing device 100, 200, and the substrate 250 therein, may emanate greater than 10 mg/day of the active agent or the volatile material. For example, in some embodiments, the substrate 250 may emanate the active agent or the volatile material at a rate greater than 10 mg/day when the airflow through the substrate 250 is increased.

Likewise, as previously discussed herein, the dosage of the substrate 250 and/or the dispensing device 100, 200 may be selected based on the desired duration of emanation, e.g., from weeks, months, or seasons. For example, if the dispensing device 100, 200 is designed to have an emanation rate of about 2 mg active agent/day then a dispensing device 100, 200 designed for use for one month will be dosed with at least 60 mg of an active agent (e.g., transfluthrin). As another example, if the dispensing device 100, 200 is designed to have an emanation rate of about 2 mg active agent/day, then a dispensing device 100, 200 designed for use for three months (i.e., for a season) will be dosed with at least between about 1,500 and about 2,300 mg of an active agent (e.g., transfluthrin). Hence, initial dosage level of the volatile material and/or the active agent therein may vary from 1 mg to 5 g and may be dependent on the properties of the substrate 250, a desired emanation rate, and/or a desired emanation lifetime.

As discussed above, in some embodiments, the dispensing device 100, 200 may be initially dosed with the volatile material and/or the active agent with a predetermined initial dosage. In particular aspects, the initial dosage of the volatile material and/or the active agent therein may range between about 1 mg and about 5 g, between about 20 mg and about 3 g, between about 20 mg and about 1 g, between about 20 mg and about 200 mg, between about 40 mg and about 100 mg, or between about 55 mg and about 70 mg. In other aspects, the initial dosage of the volatile material and/or the active agent therein may range between about 1 mg and about 5 g, between about 1 g and about 3 g, or between about 1.5 g and about 2.3 g. In one example, a dispensing device 100, 200 or the substrate 250 may be initially dosed with about 75 mg of an active agent. In another example, the dispensing device 100, 200 or the substrate 250 may be initially dosed with between about 3 g and about 4.6 g of a volatile material, which may include approximately between about 1.5 g and 2.3 g of an active agent (e.g., transfluthrin or metofluthrin) and approximately between about 1.5 g and about 2.3 g of a diluting agent (e.g., Exxsol™ D60). In this particular embodiment, the initial dose is delivered per 230 cm$^2$ of material (e.g., between about 3 g and about 4.6 g of a volatile material per 230 cm$^2$ of the substrate 250). Further, in these embodiments, the inclusion of a diluting agent may promote faster wicking, better distribution, and may inhibit crystallization.

After the substrate 250 is dosed with an amount of volatile material, the substrate 250 is placed within the dispensing device 100, 200, which prevents contact between a future user of the dispensing device 100, 200 and the active agent. Further, the dispensing device 100, 200 and the apertures 120, 130, thereof, promote the appropriate airflow to allow for protective emanation of the volatile material from the dispensing device 100, 200.

Although amounts of an initial dosage are outlined above with regard to particular embodiments, it should be understood by one skilled in the art that the initial dosage may vary and may be dependent on a combination of factors, including but not limited to, the surface area of the substrate 250 to which the volatile material is applied, the properties of the one or more layers of the substrate 250 to which the volatile material may be applied (e.g., a thickness of the first layer 252, the second layer 254, or the third layer 256), a desired delivery rate of the volatile material from the dispensing device 100, 200, a type of material(s) used for the one or more layers of the dispensing device 200 (e.g., a type of material(s) used for the first layer 252, a type of material(s) used for the second layer 254, a type of material(s) used for the third layer 256), or a type of volatile material(s) used in the dispensing device 100, 200.

EXAMPLES

The examples herein are intended to illustrate certain embodiments of the dispensing device 100, 200 or the substrate 250 to one of ordinary skill in the art and should not be interpreted as limiting in the scope of the disclosure set forth in the claims. The dispensing device 100, 200 or the substrate 250 may comprise the following non-limiting examples.

In connection with the examples herein, the emanation rates and the amount of active agent, e.g., an amount of transfluthrin, remaining in the substrate of the examples herein were measured by analyzing the weight loss of a particular substrate over time. More particularly, the amount of active agent remaining within a particular substrate may be calculated by first measuring the substrate 250 prior to dosing the substrate 250 with the active agent (or volatile material) and then subtracting that value from the weight of the substrate 250 at any given time after dosing. For example, with reference to Example 1, an initial weight of the substrate 250 was measured, the substrate 250 was dosed with an active agent (i.e., transfluthrin or metofluthrin), and a weight of the substrate 250 was measured multiple times after initial dosage and after emanation of the active agent into the ambient environment. The initial weight of the substrate 250 was then subtracted from a weight of the substrate 250 after initial dosage and this value indicated the remaining active agent within the substrate 250. Further, after determining the remaining active agent within the substrate 250, the amount of active agent (or volatile material) emanated to the ambient environment may also be calculated by subtracting the amount of active agent remaining in the substrate 250 from the initial dosage amount of the active agent. All weight measurements can be performed on an analytical scale. Further, the examples herein were conducted in a closed environment, such as a sealed chamber, having a controlled airflow rate.

Example 1

As discussed herein, characteristics relevant to the dispensing device 100, 200 and the substrate 250 may be altered to provide optimal emanation of a volatile material from the dispensing device 100, 200. Additionally, according to an aspect of the present disclosure, the characteristics of the dispensing device 100, 200 and the substrate 250 may be altered to provide an optimal, as well as constant, emanation of a volatile material or active agent.

To demonstrate the consistent emanation rate of a volatile material from substrates of the present disclosure, a substrate 250 having a surface area of approximately 30 cm$^2$ was dosed with about 75 mg of two different volatile materials and the emanation rate was measured over a 40 day period. The data collected is depicted in FIG. 13.

In this example, the substrate 250 includes three layers, such as the first layer 252, the second layer 254, and the third layer 256. Further, in this embodiment, the first layer 252 is a woven material having a honeycomb weave pattern, a pore size of 3 mm and a thickness of 0.3 mm; the second layer 254 is a fibrous material constructed from polyester thread and the substrate 250 has a surface density of about 340 g/m$^2$; and the third layer 256 is a woven material having a honeycomb weave pattern, a pore size of 3 mm and a thickness of 0.3 mm.

Figure 13:
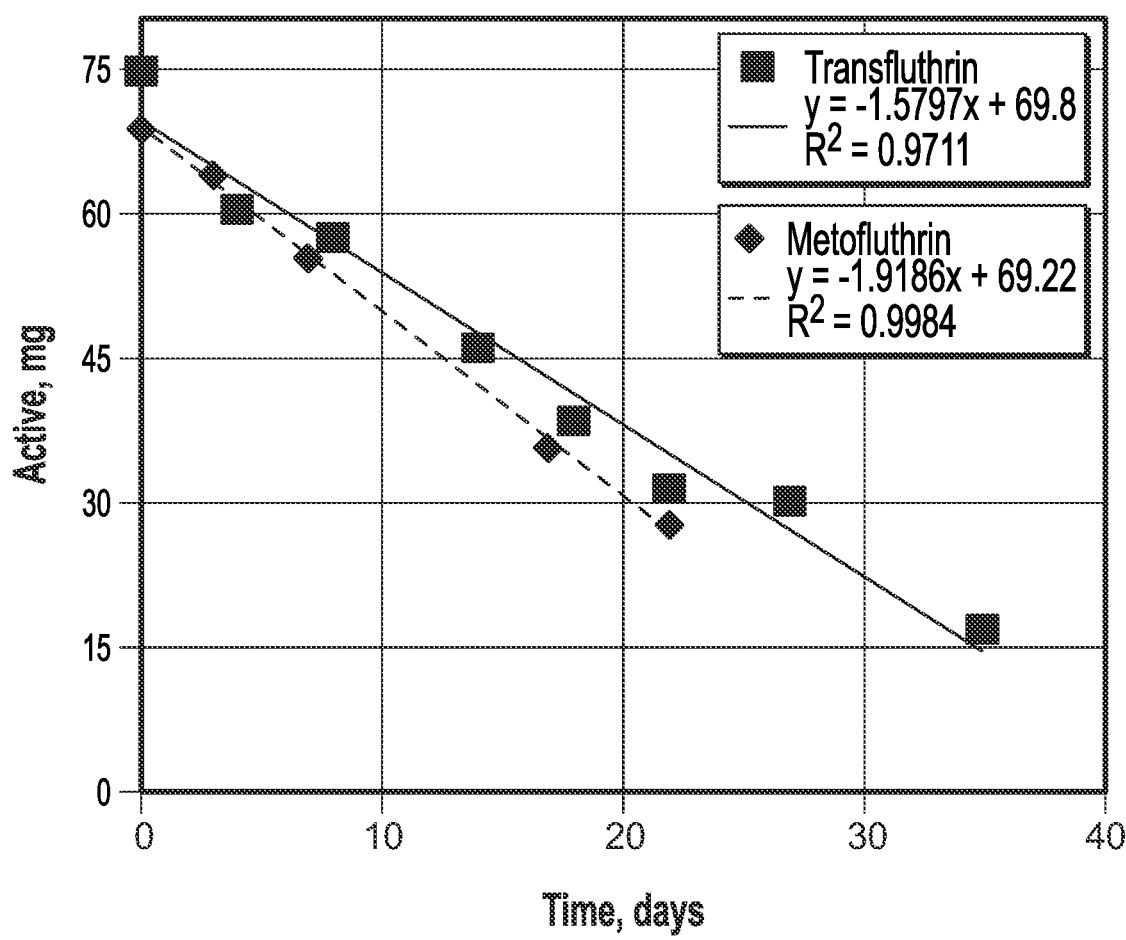
FIG. 13 is a graph illustrating the release or emanation rate of a plurality of active agents of a volatile material from the substrate of FIG. 9, according to an aspect of the present disclosure, over a period of time.

As shown in FIG. 13, a linear release rate was observed when the substrate 250 was dosed with approximately 75 mg of transfluthrin or 75 mg of metofluthrin. When the substrate 250 was dosed with transfluthrin, the substrate 250 constantly emanated the volatile material over a month and, in particular, approximately 36 days at a constant linear rate of about 1.5 mg/day. When the substrate 150 was dosed with metofluthrin, the substrate 250 emanated the volatile material over 20 days at a constant linear rate of about 1.9 mg/day. As a result, embodiments of the substrate 250 may be effectively employed to provide a constant, linear release rate of a volatile material that is long lasting. Further, the degree of volatile material and the characteristics of the substrate 250 (e.g., surface area, porosity, thickness, density, etc.) may be varied dependent on the dosage. For example, the characteristics of the substrate 250 may be altered such that higher dosages (e.g., dosages between about 150 mg and about 800 mg) may be applied to the substrate 250 to provide linear release rates of a volatile material over longer periods of time, such as 3 to 6 months, or even 12 months.

As previously discussed herein, the materials used for the substrate 250, and the layers thereof, may be chosen to optimize the characteristics of the substrate 250, including the saturation level or emanation rate of the substrate 250. Optimal materials for the substrate 250, and the first and third layers 252, 256, are shown in Table 1 below and were provided by Gehring-Tricot Warp Knit Fabrics located in St. Johnsonville, New York and Dolgeville, New York, with the exception of the "SCJ 1.0" sample, which is a substrate similar to the substrate described in U.S. patent application Ser. No. 15/164,580, the entire contents of which is incorporated herein by reference. More particularly, based on the desired emanation rate, initial dose of a volatile material, and period of desired emanation, an optimal material for the substrate 250 may be chosen. For example, if a 0.15 mg/hr emanation rate is desired over a 40 day period, SHR 714 F may be chosen for the first layer 252 and/or the third layer 256 of the substrate 250 and the substrate 250 may be dosed with approximately 147 mg of volatile material.

Figure 14:
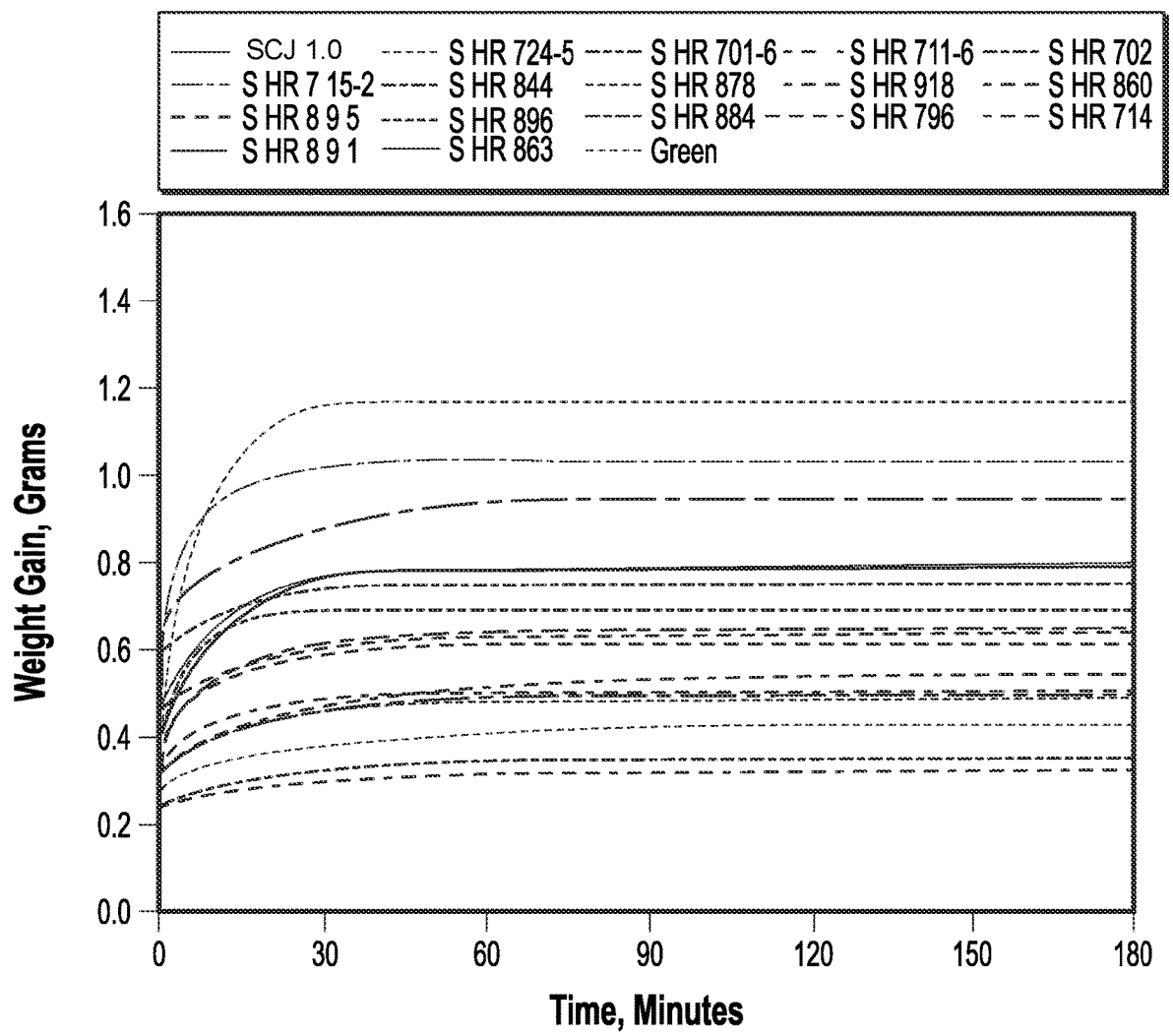
FIG. 14 is a graph illustrating the wicking rate of various substrates over a period of time.

Additionally, FIG. 14 illustrates the wicking rate of each material listed in Table 1 as a function of time, and after approximately 1.2 grams of volatile material was applied to the material.

TABLE 1

Saturation Levels of 3-D Meshes

| Sample ID | Saturation (mg) | Thickness (mm) | Wicking time (min) | | | Release Rate (mg/hr) |
|---|---|---|---|---|---|---|
| | | | $T_{25\%}$ | $T_{50\%}$ | $T_{75\%}$ | |
| SHR 714 F | 147 | 0.3 | 11.3 | 40.9 | 1033 | 0.15 |
| Gehring Green Mesh | 146 | 2.35 | 3.8 | 17.2 | 41.4 | 0.14 |
| SCJ 1.0 | 129 | 2.35 | 2.2 | 10.5 | 26.7 | 0.13 |
| SHR 796 F | 187 | 0.3 | 2.7 | 9.6 | 24.2 | 0.12 |
| SHF 918 | 194 | 1.74 | 1.5 | 6.2 | 17.1 | 0.12 |
| SHR 891 | 241 | 1.72 | 2.4 | 10.5 | 29.8 | 0.11 |
| SHR 896 | 496 | 1.76 | 1.3 | 5.5 | 15.4 | 0.11 |
| SHR 701/6 | 310 | 2 | 0.7 | 2.6 | 7 | 0.1 |
| SHR 711/6 | 221 | 1.9 | 2.3 | 13.5 | 46 | 0.09 |
| SHR 878 | 717 | 2.96 | 1 | 4.1 | 11.1 | 0.09 |
| SHR 863 | 292 | 2.39 | 6.7 | 6.4 | 17.5 | 0.08 |
| SHR 884 | 247 | 2.58 | 1.3 | 4.9 | 14.3 | 0.07 |
| SHR 895 | 307 | 1.39 | 0.4 | 3.2 | 12.8 | 0.07 |
| SHR 844 | 270 | 4.38 | 1.6 | 8 | 24.6 | 0.06 |
| SHR 860/1 | 368 | 5.14 | 2.3 | 12 | 33.2 | 0.05 |
| SHR 724/5 | 184 | 1.35 | 2.7 | 9.3 | 27.8 | 0.04 |
| SHR 702/1 | 372 | 0.3 | 1.17 | 4.2 | 10.8 | 0.01 |

Example 2

To demonstrate the consistent emanation rate of a volatile material from substrates of the present disclosure used in combination with the dispensing device 200, and over a period exceeding one month, a substrate 250 was inserted into the dispensing device 200 and the emanation rate of the substrate 250 was measured. In this example, the substrate 250 includes three layers, such as the first layer 252, the second layer 254, and the third layer 256. Further, in this embodiment, the first layer 252 is a woven material having a honeycomb weave pattern, a pore size of 3 mm and a thickness of 0.3 mm; the second layer 254 is a fibrous material constructed from polyester and the substrate 250 has a surface density of about 340 g/m$^2$; and the third layer 256 is a woven material having a honeycomb weave pattern, a pore size of 3 mm and a thickness of 0.3 mm. The substrate 250 was dosed with about 2400 mg of transfluthrin and the concentration of the transfluthrin within the substrate 250 at different locations in a sealed chamber was measured over a period of 75 days. During this trial, the substrate 250 was exposed to an airflow of about 4.8 meters/minute. The data collected is shown in FIGS. 15A, 15B, and 15C.

Figure 15A:
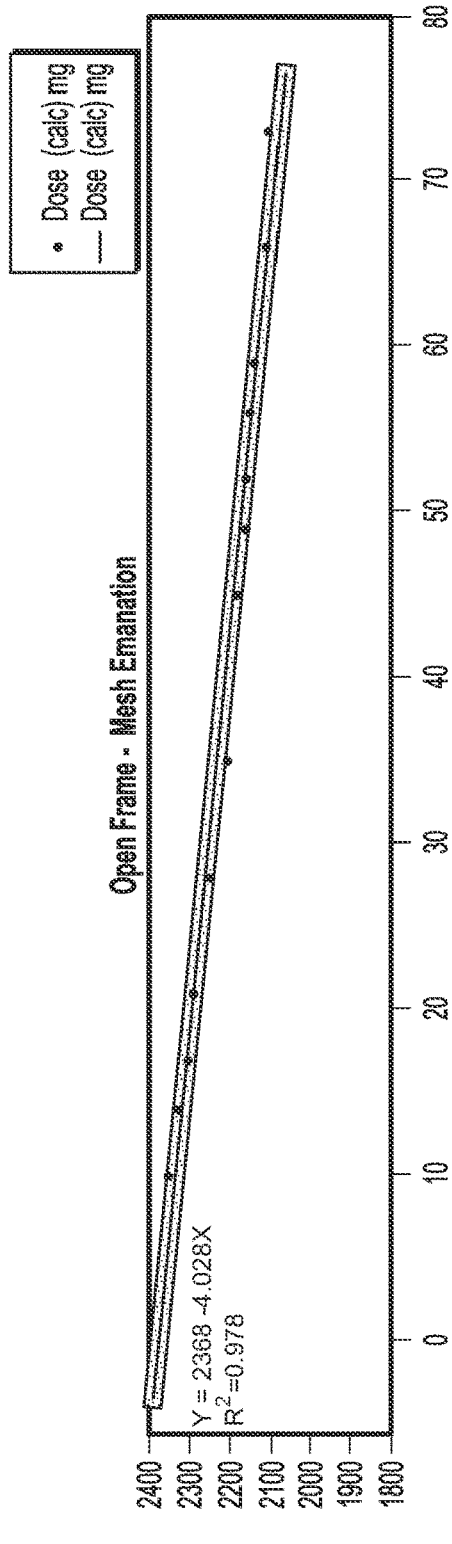
FIG. 15A is a graph illustrating the release or emanation rate of an active agent of a volatile material from the dispenser of FIG. 6 having the substrate of FIG. 9 over a period of time.
Figure 15B:
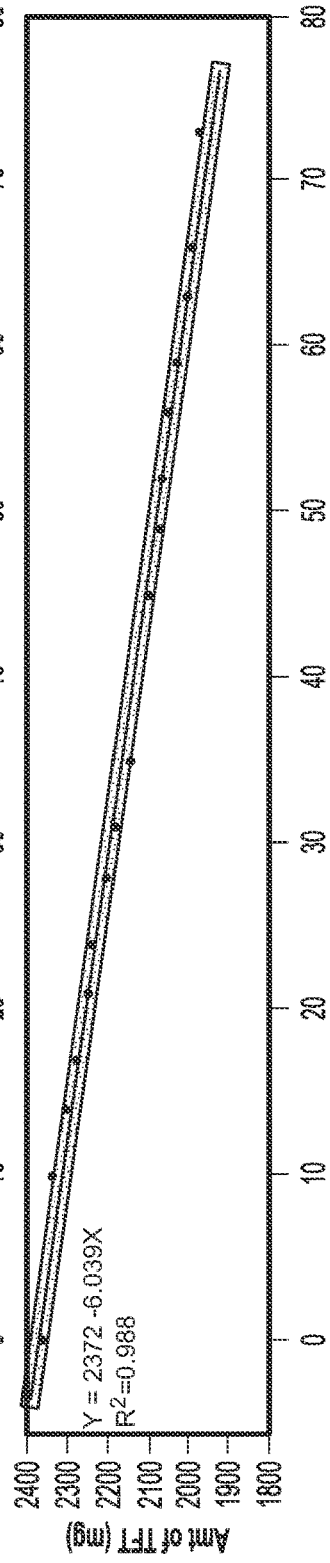
FIG. 15B is another graph illustrating the release or emanation rate of an active agent of a volatile material from the dispenser of FIG. 6 having the substrate of FIG. 9 over a period of time.
Figure 15C:
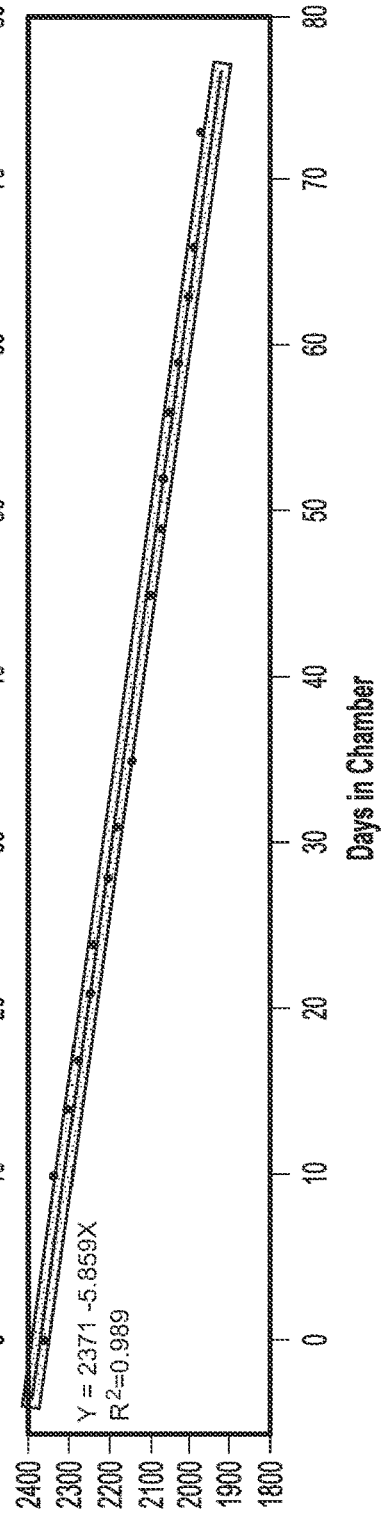
FIG. 15C is another graph illustrating the release or emanation rate of an active agent of a volatile material from the dispenser of FIG. 6 having the substrate of FIG. 9 over a period of time.

As shown in FIGS. 15A-15C, the dispensing device 200 having the substrate 250 constantly emanated a volatile material over a period of 75 days, and emanated the active agent (i.e., transfluthrin) at a constant rate between about 4 mg/day and 6 mg/day. FIG. 15A depicts the concentrations of the active agent within the substrate 250 of the dispensing device 200, wherein the dispensing device 200 was at a first location within a sealed chamber. At this location, the dispensing device 200 (or substrate 250) constantly emanated about 4 mg/day for a period greater than 70 days. FIG. 15B depicts the concentrations of the active agent within the substrate 250 of the dispensing device 200, wherein the dispensing device 200 was at a second location within the sealed chamber. At this location, the dispensing device 200 (or substrate 250) constantly emanated about 6 mg/day for a period greater than 70 days. Finally, FIG. 15C depicts the concentrations of the active agent within the substrate 250 of the dispensing device 200, wherein the dispensing device 200 was at a third location within the sealed chamber. At this location, the dispensing device 200 (or substrate 250) constantly emanated about 4 mg/day for a period greater than 70 days.

As shown in FIGS. 15A-C, the substrates 250 of the present disclosure have the ability to release a volatile material or active agent, such as transfluthrin, over a prolonged period of time. In this particular example, a substrate 250 was designed to emanate a volatile material having transfluthrin as an active agent to repel insects (e.g., mosquitos) over a prolonged period of time without the need to replace or re-dose the substrate 250. Looking to FIGS. 15A-15C, the substrate 250 used in this particular example was able to be saturated with about 2400 mg of transfluthrin and released transfluthrin at an emanation rate ranging between about 4 mg/day and 6 mg/day. Additionally, the emanation rate was constant over the 75 day period, as shown by the fitted linear regression lines having high correlation values (i.e., $R^2$ values) of 0.978, 0.988, and 0.989. Using these linear regression lines, it can be determined that the substrate 250 disclosed herein provide constant emanation of an active agent, such as transfluthrin, over a prolonged period of time greater than about one month, two months, three months, etc. More particularly, using the linear regression lines, the substrate 250 of the present embodiment has the capability of emanating the active agent, transfluthrin, for a period exceeding one year at a constant, linear rate.

Example 3

Multiple characteristics and dimensions of the substrate 250 were altered to demonstrate the effect the characteristics have on the release or emanation rate of a volatile material from the substrate 250.

First, the thickness of the substrate 250 was varied by varying the thickness of the layers thereof (e.g., second layer 252), and the percentage of volatile material (i.e., transfluthrin) remaining in the substrate 250 after 72 hours was measured. The data collected is depicted in FIG. 16.

Second, the pore diameter of the first layer 252 of the substrate 250 was varied and the percentage of volatile material remaining in the substrate 250 after 72 hours was measured. The data collected is depicted in FIG. 17.

Third, the pore diameter of the third layer 256 of the substrate 250 was varied and the percentage of volatile material remaining in the substrate 250 after 72 hours was measured. The data collected is depicted in FIG. 18.

Figure 16:
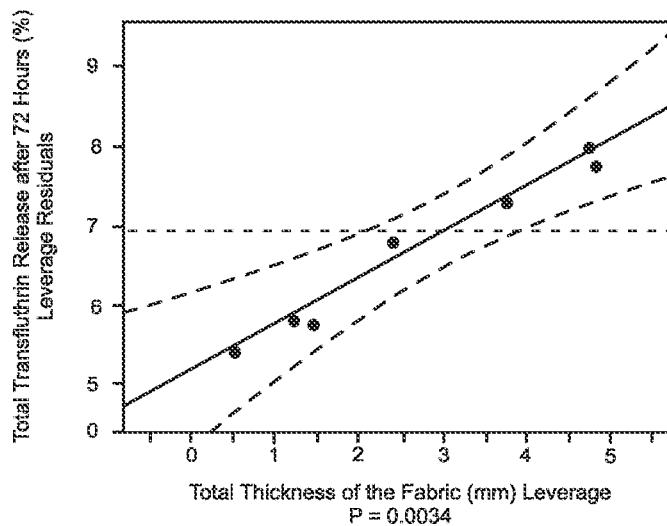
FIG. 16 is a graph illustrating an amount of an active agent within a variety of substrates having varying thickness, after 72 hours.
Figure 17:
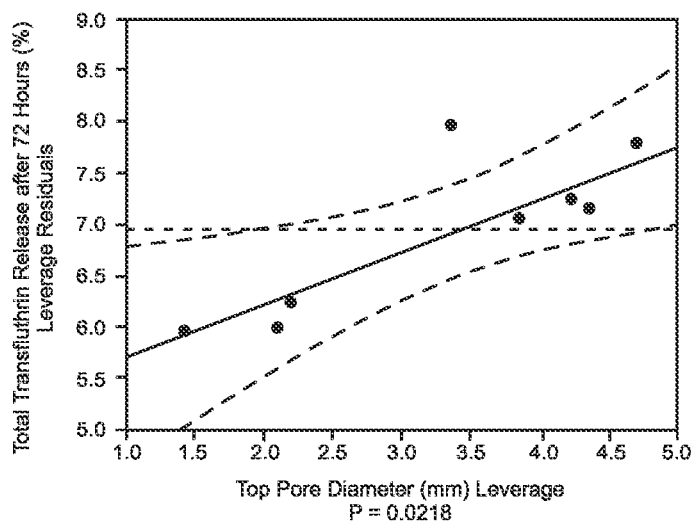
FIG. 17 is a graph illustrating an amount of an active agent within a variety of substrates having varying pore diameters, after 72 hours.
Figure 18:
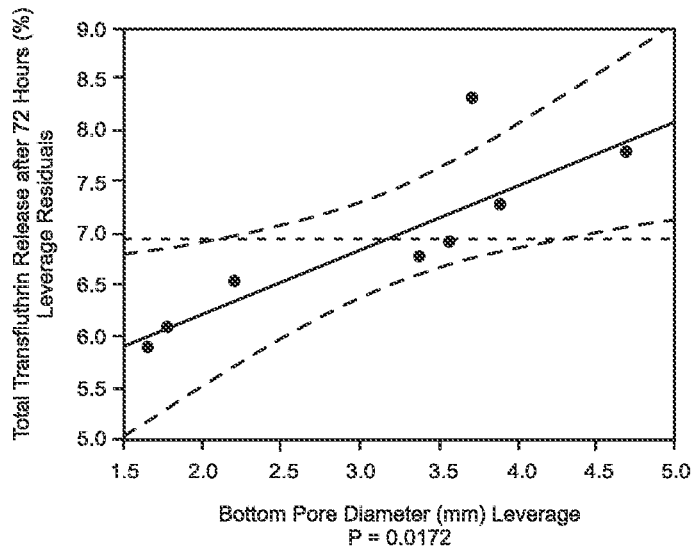
FIG. 18 is a graph illustrating an amount of an active agent within a variety of substrates having varying pore diameters, after 72 hours.

As shown in FIGS. 16-18, the release rate of the volatile material from the substrate 250 was positively and linearly correlated to the thickness of the substrate 250, the pore size of the first layer 252, and the pore size of the third layer 256 of the substrate 250.

A statistical analysis was also conducted, which is shown in Tables 2 and 3. As shown in Tables 2 and 3, a high correlation value of approximately 0.9 was determined between the thickness and pore size of the first layer 252 and the second layer 254, and the release rate of the volatile material from the substrate 250. Further, the F ratio was minimal.

TABLE 2

| Summary of Fit | |
|---|---|
| R Square | 0.907165 |
| R Square Adj. | 0.851464 |
| Root Mean Square Error | 0.521671 |
| Observations (or Sum Wgts) | 9 |

TABLE 3

| Analysis of Variance | | | | |
|---|---|---|---|---|
| Source | DF | Sum of Squares | Mean Square | F Ratio |
| Model | 3 | 13.296522 | 4.43217 | 16.2864 |
| Error | 5 | 1.360701 | 0.27214 | Prob > F |
| C. Total | 8 | 14.657222 | | 0.0052* |

Example 4

Figure 19:
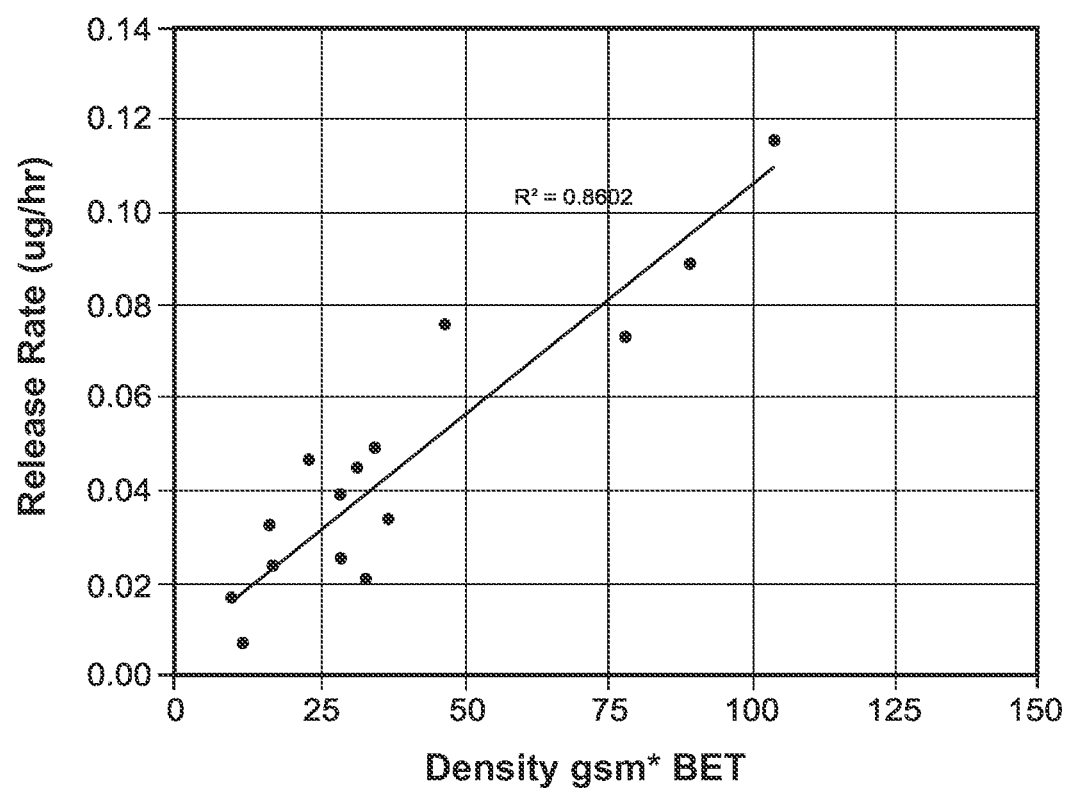
FIG. 19 is a graph illustrating the release or emanation rate of an active agent of a volatile material from a variety of substrates having varying densities and fiber surface areas.

As previously discussed herein, characteristics relevant to the dispensing device 100, 200 and the substrate 250 may be altered to provide optimal emanation of a volatile material from the dispensing device 100, 200. According to another aspect of the present disclosure, the surface area/density of the substrate 250 was varied to demonstrate the effect the surface area/density had on the emanation or release rate of a volatile material from the substrate 250. More particularly, the surface density of a substrate 250 was varied, by altering the layers of the substrate 250, between about 10 $m^2$/bulk $m^2$ and about 100 $m^2$/bulk $m^2$ and the release or emanation rate from the substrates were measured. The data collected is depicted in FIG. 19. Further, as shown in FIG. 19, a positive and linear relationship was observed between the surface density of the substrate 250 and the release rate of a volatile material therefrom. The correlation of release rate with density ($g/m^2$ or GSM)×surface area BET (i.e., actual $m^2$/bulk $m^2$) provides directional guidance on a method of selecting commercially available meshes for the substrate 250 to provide and target the desired release rate or emanation rate for a particular application that will use the substrate 250.

With continued reference to FIG. 19, $g/m^2$*BET is a representation of an amount of surface area available for a given unit of volume, i.e., a low value corresponds to a small amount of surface area corresponding to a given volume of the substrate 250 and a high value corresponds to a large amount of surface area corresponding to a given volume of the substrate 250. Further, BET refers to the Brunauer-Emmett-Teller theory, which is an analysis technique for measurement of the specific surface area of a material, such as the substrate 250, and more particularly, the surface area of the fibers ($m^2$/g) per mass of sample. The results shown in FIG. 19 exemplify a linear relationship between the amount of surface area available and the release rate (or emanation rate) of the active agent or volatile material within the substrate 250. In short, as $g/m^2$*BET increases, so does the emanation rate.

Example 5

Figure 20:
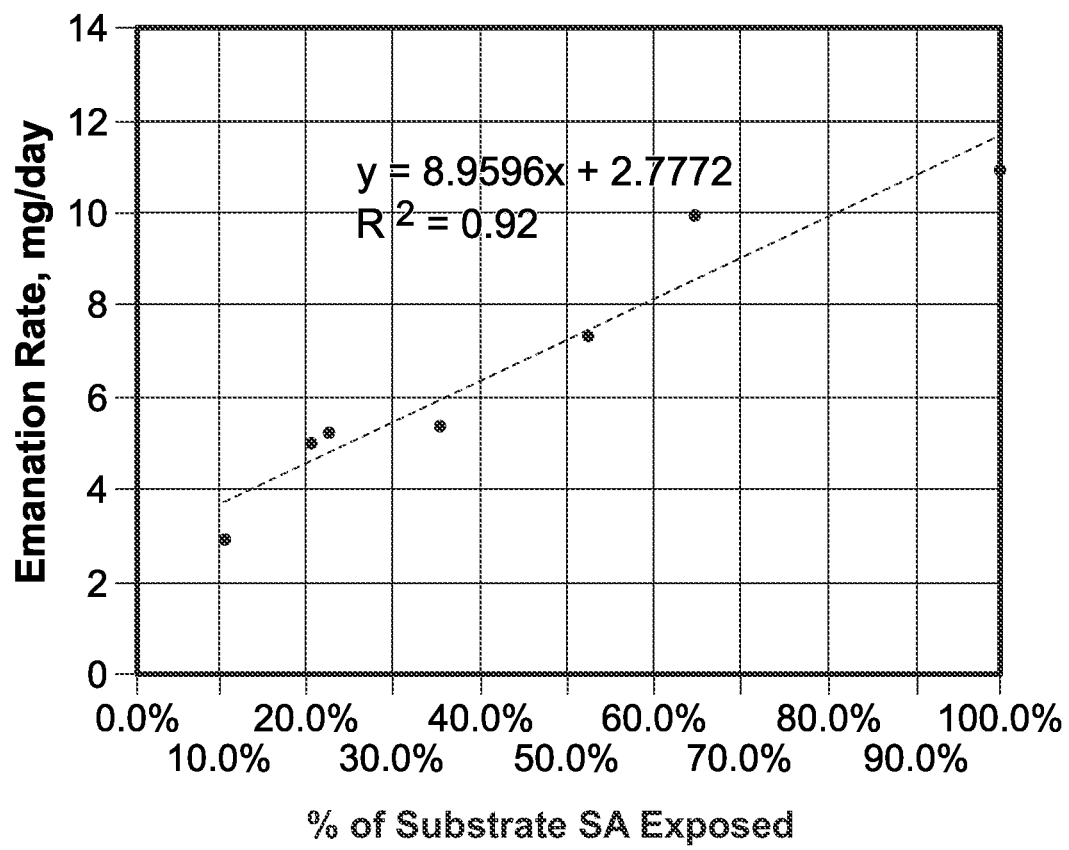
FIG. 20 is a graph illustrating the release or emanation rate of an active agent of a volatile material from a variety of dispensers having varying percentages of the substrate exposed during use thereof.

As further discussed herein, the percentage of the substrate 250 exposed may alter the emanation of the volatile material from the dispensing device 100, 200. Therefore, according to another aspect of the present disclosure, the percentage of the surface areas of the substrate 250 exposed was varied to demonstrate the effect the percent exposure had on the emanation or release rate of a volatile material from the substrate 250. More particularly, the percentage of the substrate 250 exposed was varied between about 10% and about 100% and the release rate from the substrates were measured. The data collected is depicted in FIG. 20. Further, as shown in FIG. 20, a positive and linear relationship was observed between the percent exposure of the surface area of the substrate 250 and the release rate of a volatile material therefrom.

Method of Producing the Substrate

All of the findings herein can be utilized to optimize the substrate 250 and produce a substrate 250 for constant, passive emanation of a volatile material over a specified period of time. Further, the substrate 250, and the layers thereof, may be altered or tuned to provide a substrate 250 for particular uses.

Figure 21:
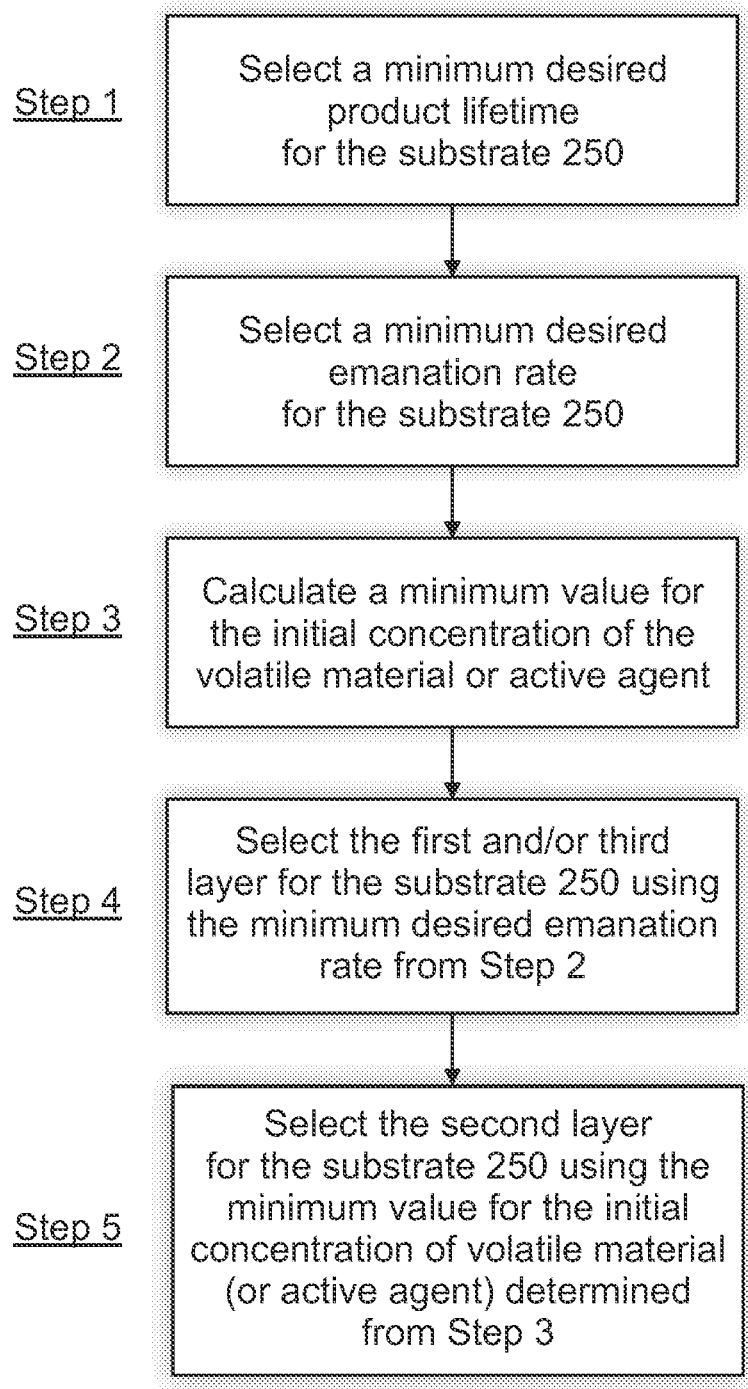
FIG. 21 illustrates a design method for constructing the substrate of FIG. 9, according to an aspect of the present disclosure.

A design method has been developed to determine the material and characteristics required to achieve the desired emanation rate and product lifetime for the substrate 250. FIG. 21 schematically illustrates the design method for constructing the substrate 250.

First, as supported by the non-limiting examples herein, it is understood that the emanation of a volatile material or active agent from the substrate 250 may be modeled using a linear regression line and the concentration of volatile material within the substrate 250 at any given time can be determined using Equation 6:

$$C(t)=X-ER*t \qquad \text{(Eq. 6)}$$

where the concentration of volatile material or active agent within the substrate 250 is $C(t)$, the initial concentration or dosage of volatile material or active agent is $X$, and the desired emanation rate or release rate of the volatile material or active agent is ER.

Step 1 of the design method involves selecting a minimum, desired product lifetime for the substrate 250, or minimum, desired product lifetime for the dispensing device 100, 200 that will include the substrate 250. For example, as previously discussed herein, a dispenser having a product lifetime of a week may be desired, or alternatively, a dispenser having a product lifetime of three months may be desired.

Step 2 of the design method involves selecting a minimum desired emanation rate (ER) for the substrate 250, or dispensing device 100, 200. For example, in some embodiments herein, an emanation rate between about 1.4 mg/day and 1.6 mg/day is desired, and in other embodiments, an emanation rate between about 4 mg/day and 6 mg/day is desired.

Step 3 in designing the substrate 250, or dispensing device 100, 200, involves calculating the minimum value for the initial concentration of the volatile material or active agent. The minimum value for the initial concentration of the volatile material or active agent may be calculated using Equation 6, and plugging in the minimum desired product lifetime from Step 1 for t and the minimum desired emanation rate from Step 2 for ER. For example, if a minimum desired product lifetime of three months (i.e., 90 days) and a minimum desired emanation rate of 3.6 mg/day are chosen in Steps 1 and 2, respectively, the minimum value for the initial concentration of the volatile material or active agent will be 324 mg of active agent (e.g., transfluthrin).

Step 4 in designing a substrate 250, or dispensing device 100, 200, involves selecting the first layer 252 and/or third layer 256 for the substrate 250 that will provide the minimum desired emanation rate (ER) determined in Step 2. FIGS. 17 and 18 provide linear correlations between the pore size and emanation rate or release rate of an active agent (i.e., transfluthrin). Additionally, Table 1 herein provides average emanation or release rates for multiple fabrics produced by Gehring-Tricot Warp Knit Fabrics located in St. Johnsonville, New York and Dolgeville, New York, which can be used for the first layer 252 or the third layer 256. Using this knowledge, a fabric from Table 1 may be chosen for the first layer 252 and/or the third layer 256 to provide the desired emanation rate. For example, if an average emanation rate of 0.15 mg/hr (or 3.6 mg/day) is desired, the fabric SHR 714 F manufactured by Genring-Tricot Corporation may be chosen for the first layer 252 or the third layer 256, or the fabric SHR 884 may be chosen for the first layer 252 and the third layer 256. Alternatively, if a fabric other than the fabrics disclosed in Table 1 is desired, Table 1 may provide a basis for comparison, and FIGS. 17 and 18 may provide the necessary correlating information between a characteristic of the fabrics (e.g., pore size) and their effect on the emanation rate. Therefore, the emanation rates of other fabrics contemplated for the first layer 252 and/or third layer 256 may be approximately estimated using these values and calculations.

Step 5 in designing a substrate 250, or dispensing device 100, 200, involves selecting the second layer 254 for the substrate 250 that will provide the desired saturation capacity for the initial concentration of the volatile material or active agent determined in Step 3. For example, if the minimum value for the initial concentration of the volatile material or active agent was determined to be 324 mg of active agent, such as 324 mg of transfluthrin, a material, thickness, and density of the second layer 254 may be altered, such that the second layer 254 can hold 324 mg of active agent therein.

After Steps 1-5, the substrate 250 may be constructed by combining the first layer 252 and/or third layer 256 selected in Step 4 with the second layer 254 selected in Step 5. The first layer 252, the second layer 254, and the third layer 256 may be combined using methods know in the art, including glue, adhesive, or the like. In other embodiments, the fibers of the second layer 254 may be interwoven with the fibers of the first layer 252 and/or the fibers of the second layer 256. In these particular embodiments, the fibers of the first layer 252, the fibers of the second layer 254, and the fibers of the third layer 256 are tied together during the weaving process. More particularly, in these embodiments, the layers 252, 254, 256 may be connected during the weaving process, such that the substrate 250 (and the layers thereof) is fully constructed using a loom. In particular embodiments, the substrate 250 may be constructed using a raschel knitting machine and may be warp knit, such as a double needle bed raschel type spacer knit.

This design method may include additional steps not specifically illustrated in FIG. 21. In some embodiments, the design method may also include a step to determine the optimal wicking rate for the substrate 250. For example, a substrate 250 with a high wicking speed may be desired, and in these embodiments, Step 4 of the design method, which involves selecting the first and/or third layer 252, 254, may involve selecting a first and/or third layer 252, 254 having the desired wicking speed. To assist in this step, Table 1 discussed herein provides average wicking speeds for multiple fabrics produced by Gehring-Tricot Warp Knit Fabrics located in St. Johnsonville, New York and Dolgeville, New York, and FIG. 14 illustrates these wicking speeds over a period of time.

In other embodiments, the design method may also include a step of constructing a dispenser or dispensing device for use with the substrate 250, such as the dispensing device 100 or the dispensing device 200. As discussed previously herein, the emanation rate of a volatile material or active agent from the substrate 250 is positively and linearly correlated to the percentage of the surface area of the substrate 250 that is exposed to an ambient environment. More particularly, FIG. 20 illustrates the positive and linear correlation between the emanation rate of a volatile material from a substrate having an active agent and the percentage of a surface area of a substrate exposed to the ambient environment. Further, the dispensing devices 100, 200 disclosed herein include one or more apertures 120, 208, 210 that expose a portion of the surface area of the substrate 250 enclosed therein, and the number of apertures 120, 208, 210 and/or the size of the apertures 120, 208, 210 may be altered to increase or decrease the percentage of the surface area of the substrate 250 that is exposed to an ambient environment. Therefore, in these embodiments, an additional step of the design method may include using the minimum emanation rate for the substrate 250 determined in Step 2, and the selection of the first substrate 252 and the third substrate 256 in Step 4, to determine the percentage of surface area of the substrate 250 that is necessary to provide the desired emanation rate from Step 2. After determining the percentage of surface area of the substrate 250 that needs to be exposed to provide the desired emanation rate, the apertures 120, 208, 210 of the dispensing devices 100, 200 may be tuned to provide the desired emanation rate. It should be understood that this step may also affect Step 4, as a designer may select a particular first layer 252 and/or third layer 256 after determining the percentage of surface area of the substrate 250 that will be exposed to the ambient environment during use of the substrate 250.

Additional Dispensers

FIGS. 22-30 illustrate additional dispensing devices that may be used in combination with the substrate 250 disclosed herein.

Figure 22:
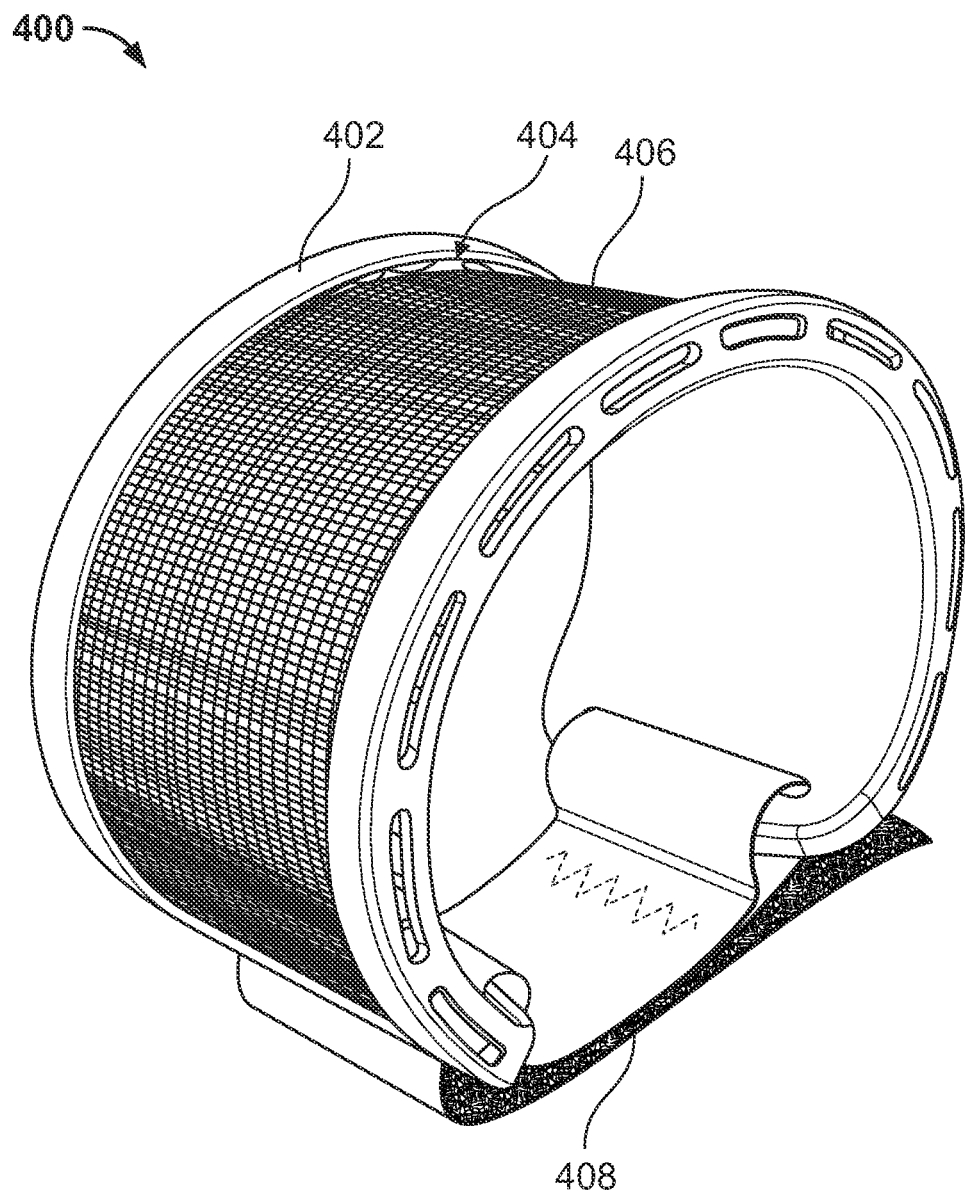
FIG. 22 is a bracelet that may be used in combination with the substrate of FIG. 9, for example.

FIG. 22 illustrates a bracelet 400 that may be used in combination with the substrate 250 of FIG. 9. In this embodiment, the bracelet 400 includes an outer frame 402 having an interior groove 404 and a recessed surface 406. A user may position the substrate 250 on the recessed surface 406 and within the groove 404. Further, the bracelet 400 may include a strap 408, such as a Velcro® strap.

Figures 23, 24:
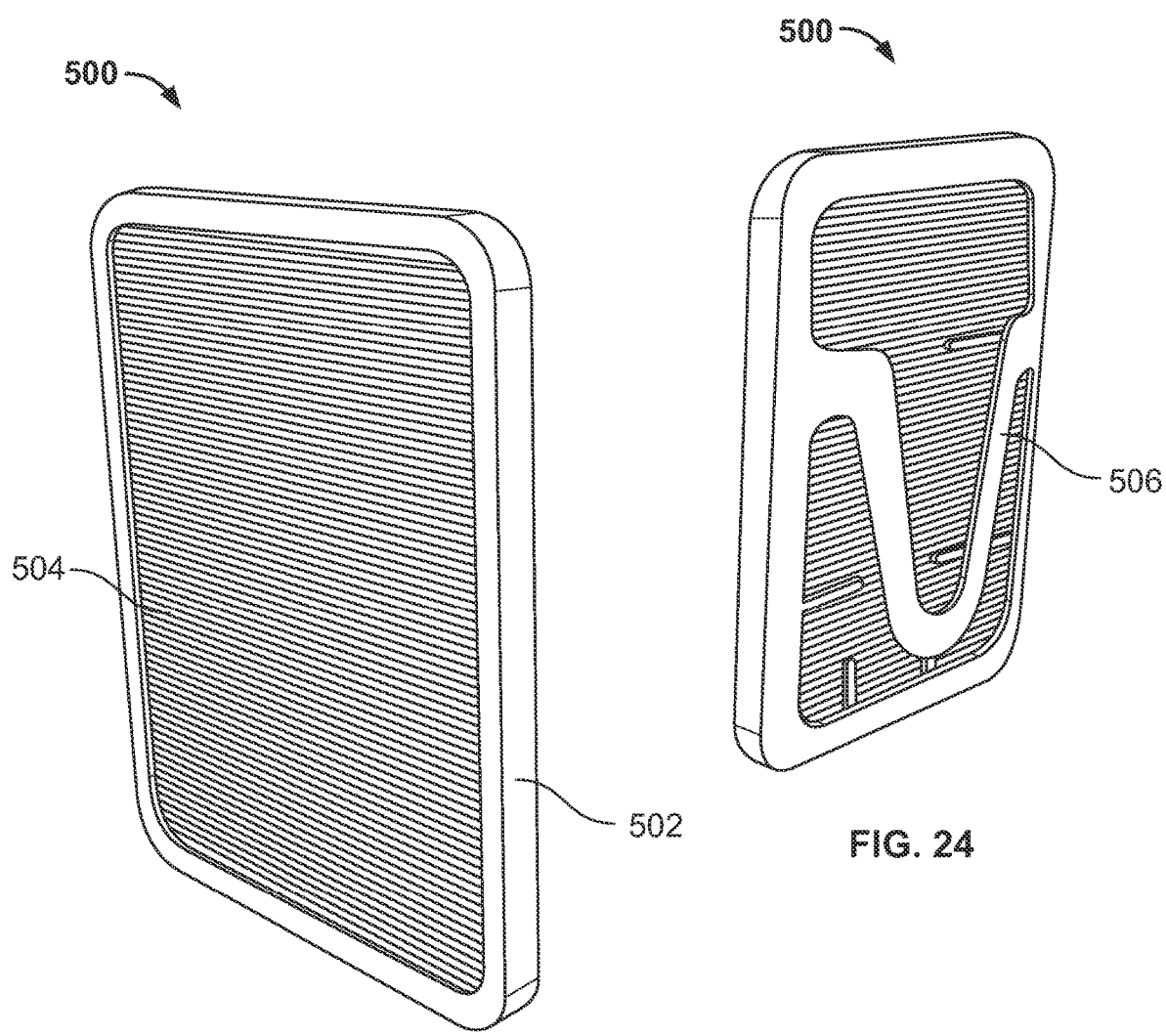
FIG. 23 is a front isometric view of a clip that may be used in combination with the substrate of FIG. 9, for example.
FIG. 24 is a rear isometric view of the clip of FIG. 23.

FIGS. 23 and 24 illustrate a dispenser 500 that may be used in combination with the substrate of FIG. 9. In this embodiment, the dispenser 500 includes an outer frame 502 and a recessed surface 504, into which the substrate 250 may be positioned. Additionally, the dispenser 500 may include a clip 506, which may be used to fix the dispenser onto a user.

Figure 25:
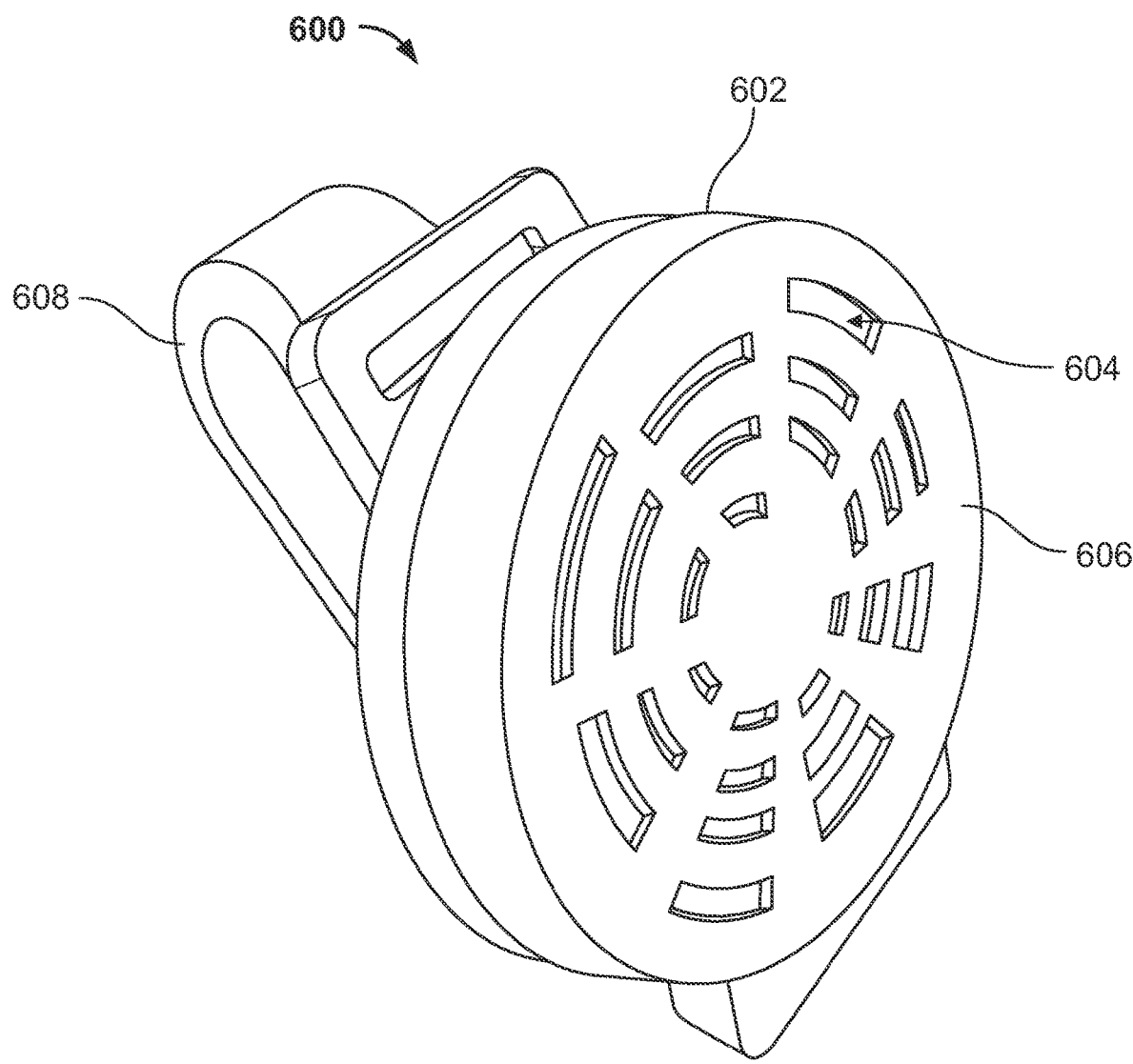
FIG. 25 is another bracelet that may be used in combination with the substrate of FIG. 9, for example.

FIG. 25 illustrates another bracelet 600 that may be used in combination with the substrate 250. In this embodiment, the bracelet 600 includes an enclosure 602 that includes a plurality of apertures 604 on a front face 606 thereof, as well as a bracelet band 608. Here, the enclosure 602 may be opened and closed, and the substrate 250 may be inserted or removed from the enclosure 602. When positioned within the enclosure, the substrate 250 may emanate a volatile material or active agent from the substrate 250 through the apertures 604.

Figure 26:
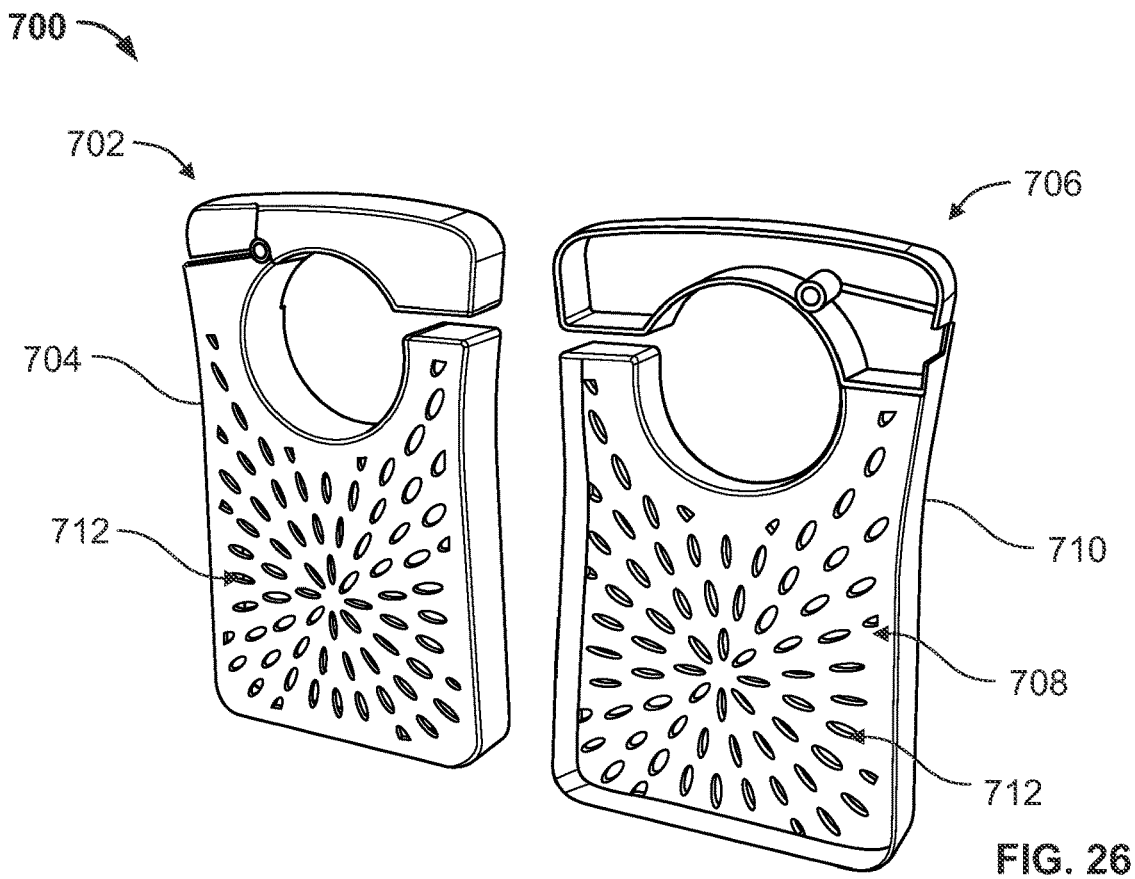
FIG. 26 illustrates a hanger that may be used in combination with the substrate of FIG. 9, for example.
Figure 27:
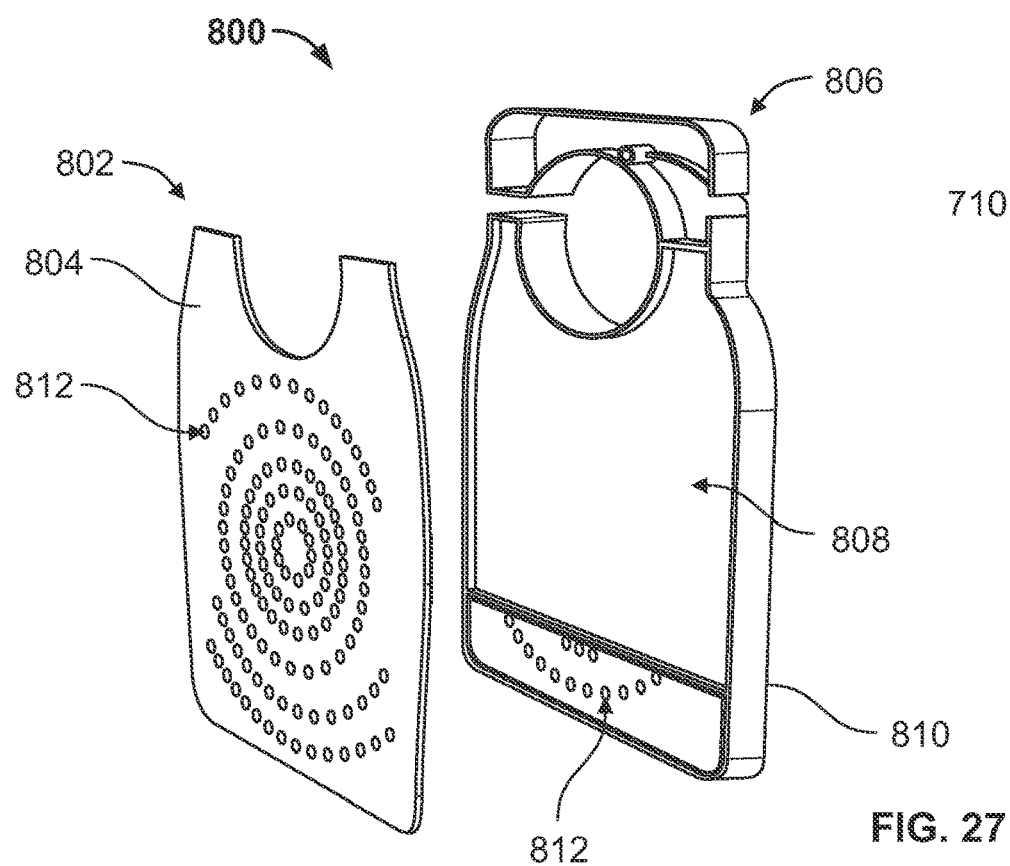
FIG. 27 illustrates another hanger that may be used in combination with the substrate of FIG. 9, for example.

FIGS. 26 and 27 illustrate two hangers 700, 800. In these embodiments, the hangers 700, 800 may include a first component 702, 802 with a front face 704, 804 that can releasably couple with a second component 706, 806 having a reservoir or recessed interior 708, 808. Further, the front face 704, 804 and a rear face 710, 810 may include a plurality of apertures 712, 812. During use, a user may insert the substrate 250 into the recessed interior 708, 808 of the second component 706, 806 and couple the first component 702, 802 to the second component 706, 806, thereby encasing the substrate 250 within the hanger 700, 800. After the substrate 250 is positioned within the hangers 700, 800, the volatile material or active agent may emanate from the substrate 250 and through the apertures 712, 812 of the hangers 700, 800.

Figure 28:
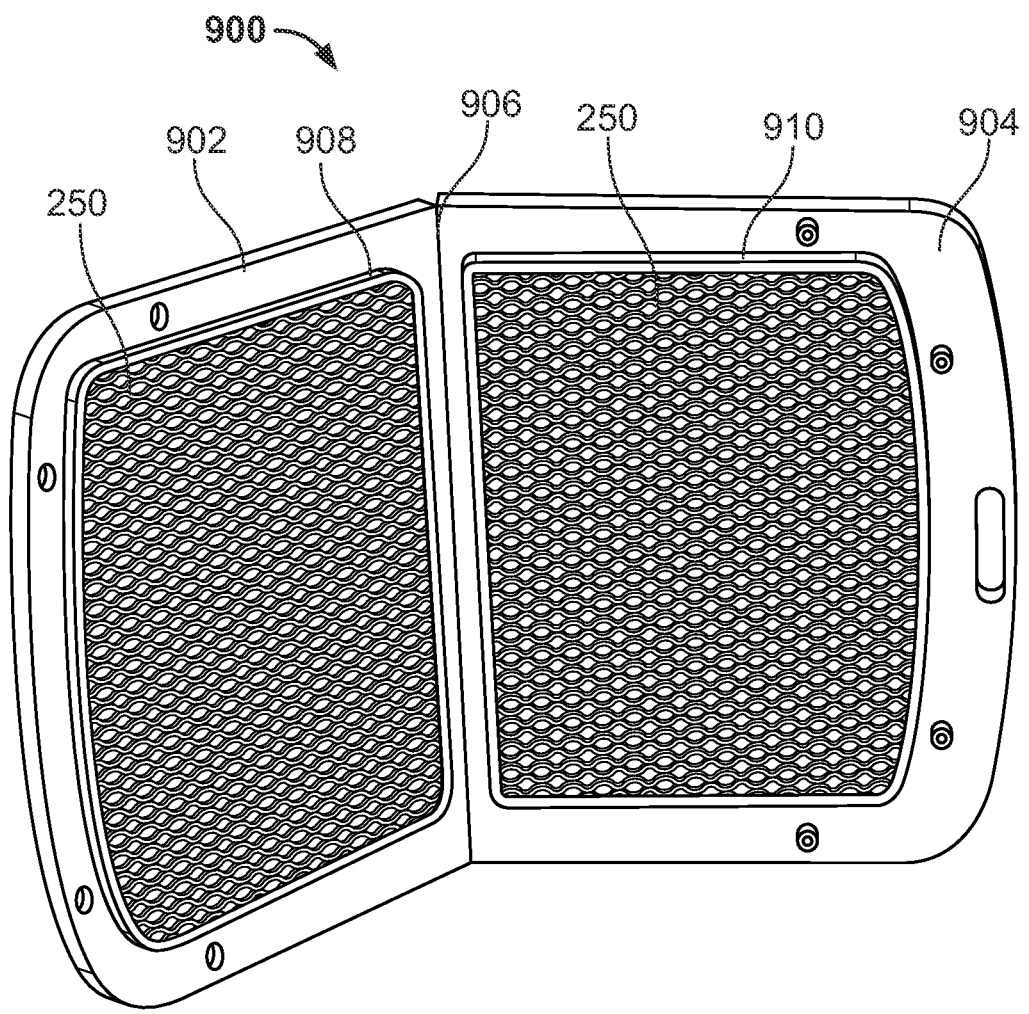
FIG. 28 illustrations a mechanism that may be used in combination with the substrate of FIG. 9, for example.

FIG. 28 depicts another dispenser 900 that may be used in combination with the substrate 250 discussed herein. In this embodiment, the dispenser 900 includes a front face 902 coupled to a rear face 904 along a hinge 906, which allows the dispenser 900 to transition between an open state, as shown in FIG. 28, and a closed state (not shown). The front face 902 includes a receptacle 908 and the rear face 904 includes a receptacle 910. Each receptacle 908, 910 may house the substrate 250 therein, and when in the open state, the dispenser 900 allows emanation of a volatile material or active agent from the substrate 250.

Figure 29:
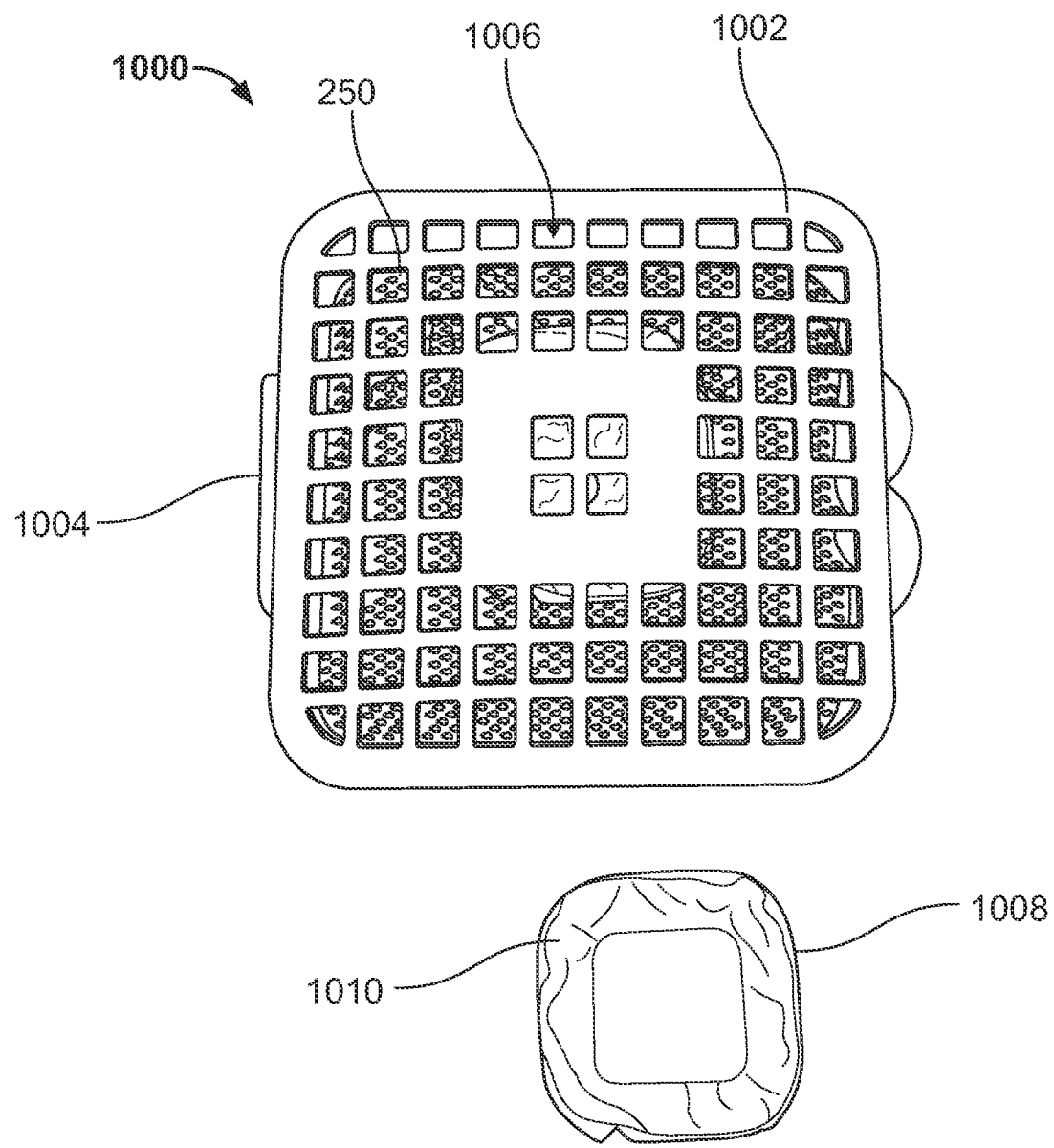
FIG. 29 illustrates a kit including a cage and pouch that may be used in combination with the substrate of FIG. 9, for example.

FIG. 29 depicts another dispenser 1000 that may be used in combination with the substrate 250. In this embodiment, similar to the dispenser 900, the dispenser 1000 includes a front face 1002 and a rear face (not shown) coupled together using a hinge 1004. Further, the front face 1002 may include a plurality of apertures 1006 which allow air to flow into the dispenser and the passive emanation of a volatile material or active agent from the substrate 250. In some embodiments, the dispenser 1000 may be provided as a kit and the kit may include a pouch 1008 that encapsulates an amount of volatile material or active agent 1010 therein. In this embodiment, the front face 1002 includes an element (not shown) on an interior surface thereof that is capable of puncturing the pouch 1008 once the dispenser 1000 is closed. Therefore, during use, a user may insert the pouch 1008 into the dispenser 1000 and close the dispenser 1000, which resultantly punctures the pouch 1008, thereby releasing the volatile material or active agent 1010 therein. After the pouch 1008 is punctured, the substrate 250 within the dispenser 1000 may wick the volatile material or active agent 1010 and subsequently emanate the volatile material or active agent 1010 therefrom over a period of time.

Figure 30:
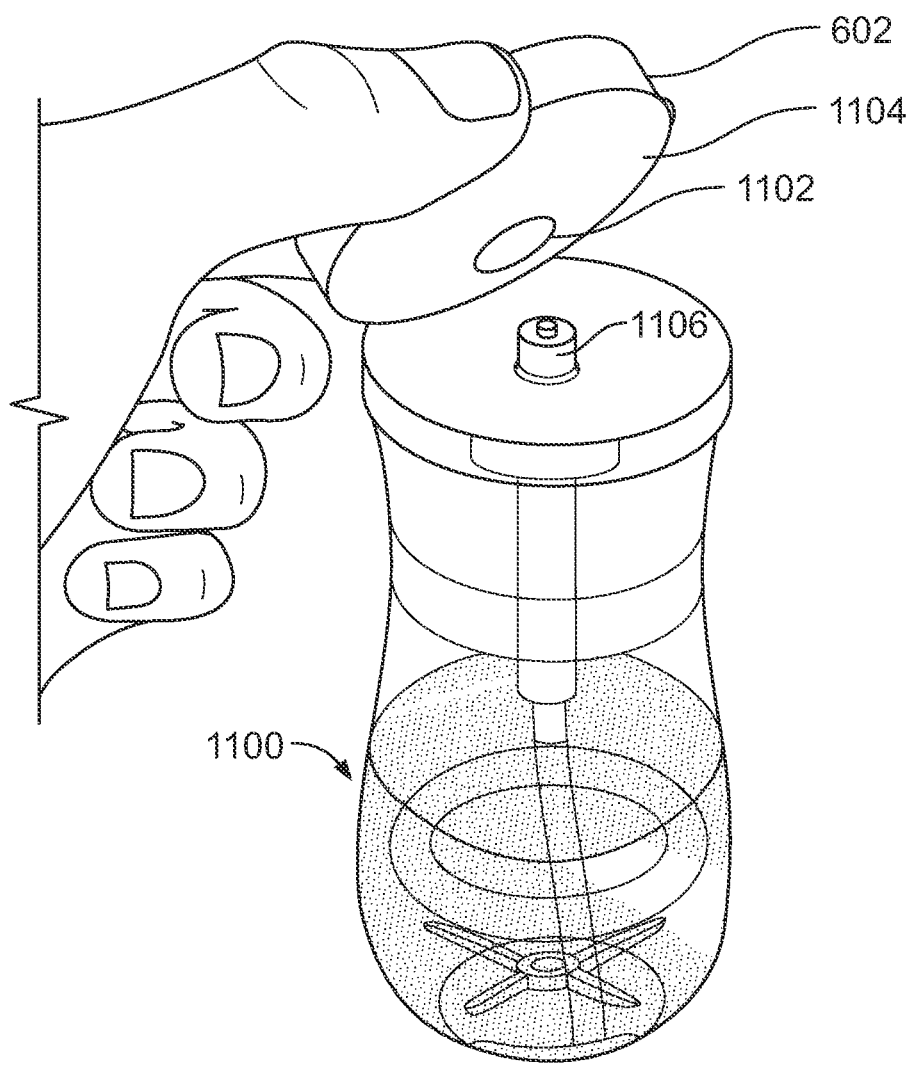
FIG. 30 illustrates a reservoir that may be used to dose the substrate of FIG. 9 or the bracelet of FIG. 25, for example.

FIG. 30 illustrates a reservoir 1100 that may be used to dose the substrate 250, or alternatively one or more of the dispensers disclosed herein. For example, the bracelet 600 may be dosed with an amount of volatile material or active agent using the reservoir 1100 by positioning an aperture 1102 on a rear side 1104 of the enclosure 602 of the bracelet 600 over a nozzle 1106. Next, a user may position the nozzle 1106 within the aperture 1102, and apply a downward force. The downward force causes the nozzle 1106 to emit an amount of volatile material from the reservoir 1100, through the nozzle 1106, and into the enclosure 602, which houses the substrate 250 therein. As a result, the substrate 250 can be re-dosed using the reservoir 1100.

Variations and modifications of the foregoing are within the scope of the present disclosure. It is understood that the embodiments disclosed and defined herein extend to all alternative combinations of two or more of the individual features mentioned or evident from the text and/or drawings. All of these different combinations constitute various alternative aspects of the present disclosure. The claims are to be construed to include alternative embodiments to the extent permitted by the prior art.

As noted previously, it will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

Any of the embodiments described herein may be modified to include any of the structures or methodologies disclosed in connection with different embodiments.

INDUSTRIAL APPLICABILITY

The aspects of the dispenser, dispensing device, or substrate described herein advantageously combine the features of a dispensing device or protective enclosure and a multi-layer substrate or mesh material to effectively emanate a volatile material or active agent at a desired time of use and over a desired amount of time. Additionally, the aspects of the dispenser or dispensing device provides a mechanism that is both easy to use and inexpensive, as well as a device that is structurally stable and safe. Accordingly, the disclosed dispenser or dispensing device may be used across a broad range of applications.

Numerous modifications to the present invention will be apparent to those skilled in the art in view of the foregoing description. Accordingly, this description is to be construed as illustrative only and is presented for the purpose of enabling those skilled in the art to make and use the invention. The exclusive rights to all modifications which come within the scope of the appended claims are reserved.

We claim:

1. A substrate for emitting a volatile material, the substrate comprising:
   a first woven layer having a first weave pattern;
   a second woven layer having a second weave pattern that is different than the first weave pattern; and
   a third layer that is disposed between the first woven layer and the second woven layer,
   wherein the substrate is configured to provide a steady state weight loss of the volatile material between about 1 mg/day and about 10 mg/day over a time of at least 30 days.

2. The substrate of claim 1, wherein the volatile material includes an active agent that is applied to at least one of the first woven layer, the second woven layer, and the third layer.

3. The substrate of claim 1, wherein the first weave pattern is a first honeycomb weave pattern and the second weave pattern is a second honeycomb weave pattern.

4. The substrate of claim 1, wherein the first weave pattern includes a first weave density, the first weave density being characterized by a first plurality of fibers of the first woven layer, and
   wherein the second weave pattern includes a second weave density, the second weave density being characterized by a second plurality of fibers of the second woven layer.

5. The substrate of claim 4, wherein the second weave density is greater than the first weave density.

6. The substrate of claim 4, wherein the third layer comprises a third plurality of fibers, the third plurality of fibers connecting at least one of the first plurality of fibers and the second plurality of fibers to form the substrate.

7. The substrate of claim 6, wherein the third layer includes a surface density between about 75 grams per square meter and about 500 grams per square meter.

8. The substrate of claim 1, wherein materials of the first and second woven layers each comprise polyester.

9. A substrate for emitting a volatile material, the substrate comprising:
   a first woven layer having a first weave pattern that includes a first weave density;
   a second woven layer having a second weave pattern that includes a second weave density; and
   a third layer that is disposed between the first woven layer and the second woven layer,
   wherein the substrate is configured to provide a steady state weight loss of the volatile material between about 1 mg/day and about 10 mg/day over a time of at least 30 days.

10. The substrate of claim 9, wherein the volatile material includes an active agent that is applied to at least one of the first woven layer, the second woven layer, and the third layer.

11. The substrate of claim 9, wherein the first weave density is characterized by a first plurality of fibers of the first woven layer and the second weave density is characterized by a second plurality of fibers of the second woven layer.

12. The substrate of claim 11, wherein the second weave density is greater than the first weave density.

13. The substrate of claim 11, wherein the third layer comprises a third plurality of fibers, the third plurality of fibers connecting at least one of the first plurality of fibers and the second plurality of fibers to form the substrate.

14. A substrate for emitting a volatile material, the substrate comprising:
   a first woven layer having a first weave pattern;
   a second woven layer having a second weave pattern that is different than the first weave pattern; and
   a third layer that is disposed between the first woven layer and the second woven layer,
   wherein the volatile material includes an active agent that is applied to at least one of the first woven layer, the second woven layer, and the third layer, and
   wherein the substrate is configured to provide a steady state weight loss of the volatile material between about 1 mg/day and about 10 mg/day over a time of at least 30 days.

15. The substrate of claim 14, wherein the first woven layer includes a first thickness and the second woven layer includes a second thickness that is different than the first thickness.

16. The substrate of claim 14, wherein the first weave pattern is a first honeycomb weave pattern and the second weave pattern is a second honeycomb weave pattern.

17. The substrate of claim 14, wherein the first weave pattern includes a first weave density, the first weave density being characterized by a first plurality of fibers of the first woven layer, and
   wherein the second weave pattern includes a second weave density, the second weave density being characterized by a second plurality of fibers of the second woven layer.

18. The substrate of claim 17, wherein the first weave density is different than the second weave density.

19. A substrate for emitting a volatile material, the substrate comprising:
- a first woven layer having a first weave pattern that includes a first weave density;
- a second woven layer having a second weave pattern that includes a second weave density; and
- a third layer that is disposed between the first woven layer and the second woven layer,
- wherein the volatile material includes an active agent that is applied to at least one of the first woven layer, the second woven layer, and the third layer, and
- wherein the substrate is configured to provide a steady state weight loss of the volatile material between about 1 mg/day and about 10 mg/day over a time of at least 30 days.

20. The substrate of claim 19, wherein the first weave density is characterized by a first plurality of fibers of the first woven layer and the second weave density is characterized by a second plurality of fibers of the second woven layer, and
- wherein the first weave density is different than the second weave density.

21. The substrate of claim 19, wherein the period of time is at least seven months.

* * * * *